United States Patent
Bales, Jr. et al.

(10) Patent No.: US 9,561,123 B2
(45) Date of Patent: *Feb. 7, 2017

(54) HIGHLY FLEXIBLE STENT AND METHOD OF MANUFACTURE

(71) Applicant: C.R. Bard, Inc., Murray Hill, CA (US)

(72) Inventors: Thomas O. Bales, Jr., Miami, FL (US); Scott L. Jahrmarkt, Miami Beach, FL (US); Charles R. Slater, Fort Lauderdale, FL (US); Peter K. Kratsch, Leander, TX (US)

(73) Assignee: C.R. Bard, Inc., Murray Hill, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/516,521

(22) Filed: Oct. 16, 2014

(65) Prior Publication Data

US 2015/0039078 A1 Feb. 5, 2015

Related U.S. Application Data

(60) Continuation-in-part of application No. 13/687,874, filed on Nov. 28, 2012, now abandoned, which is a division of application No. 12/526,690, filed as application No. PCT/US2008/053326 on Feb. 7, 2008, now Pat. No. 8,328,865, application No. 14/516,521, which is a continuation-in-part of application No. 13/970,474, filed on Aug. 19, 2013, which is a (Continued)

(51) Int. Cl.
*A61F 2/06* (2013.01)
*A61F 2/915* (2013.01)
*A61F 2/88* (2006.01)

(52) U.S. Cl.
CPC ............... *A61F 2/915* (2013.01); *A61F 2/88* (2013.01); *A61F 2002/91541* (2013.01); *A61F 2002/91575* (2013.01); *A61F 2230/0054* (2013.01); *A61F 2250/0036* (2013.01); *Y10T 29/49826* (2015.01)

(58) Field of Classification Search
CPC .. A61F 2/88; A61F 2/915; A61F 2002/91575; A61F 2002/91583; A61F 2002/91541
See application file for complete search history.

(56) References Cited

U.S. PATENT DOCUMENTS

| | | | | |
|---|---|---|---|---|
| 5,925,061 | A * | 7/1999 | Ogi | A61F 2/91 623/1.2 |
| 6,878,162 | B2 * | 4/2005 | Bales | A61F 2/88 623/1.15 |

(Continued)

*Primary Examiner* — Brian Dukert
(74) *Attorney, Agent, or Firm* — C. R. Bard Intellectual Property; Buchalter Nemer

(57) ABSTRACT

Preferred embodiments of a stent with a high degree of flexibility are shown and described. The stent can include a continuous helical winding having interconnected struts joined at vertices, and having bridges connecting sections of the helical winding to each other. An annular ring can be provided at one or both ends of the helical winding, and the annular ring can have extensions extending to connect to the helical winding. One of the extensions can connect to a bridge and another extension can connect to a vertex. The struts at the ends of the helical winding can have strut lengths that differ from the strut lengths of the struts in a central portion of the winding between the ends of the winding.

9 Claims, 16 Drawing Sheets

Related U.S. Application Data continuation of application No. 11/074,806, filed on Mar. 8, 2005, now Pat. No. 8,512,391, which is a continuation-in-part of application No. 10/231,666, filed on Aug. 30, 2002, now Pat. No. 6,878,162.

(60) Provisional application No. 60/889,421, filed on Feb. 12, 2007.

(56) References Cited

U.S. PATENT DOCUMENTS

| | | | |
|---|---|---|---|
| 2003/0176914 A1* | 9/2003 | Rabkin | A61F 2/91 623/1.15 |
| 2006/0074480 A1* | 4/2006 | Bales | A61F 2/88 623/1.15 |

* cited by examiner

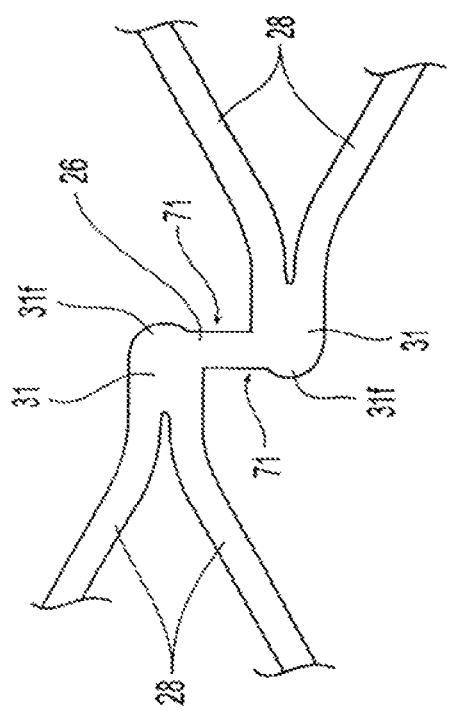
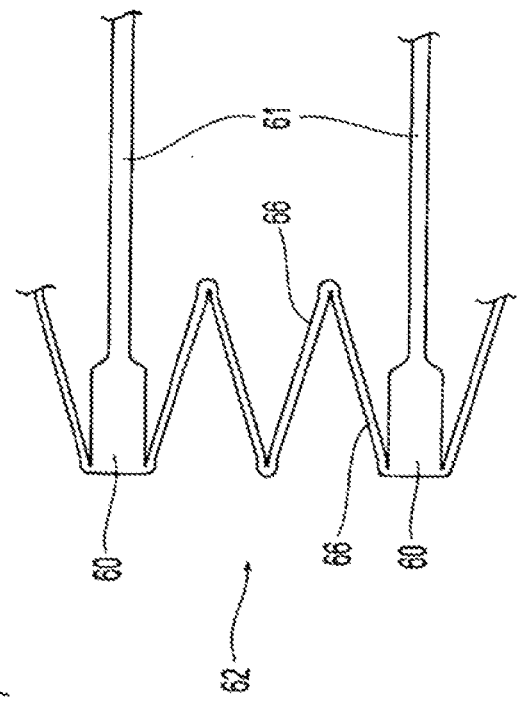
Fig. 4
Fig. 5A

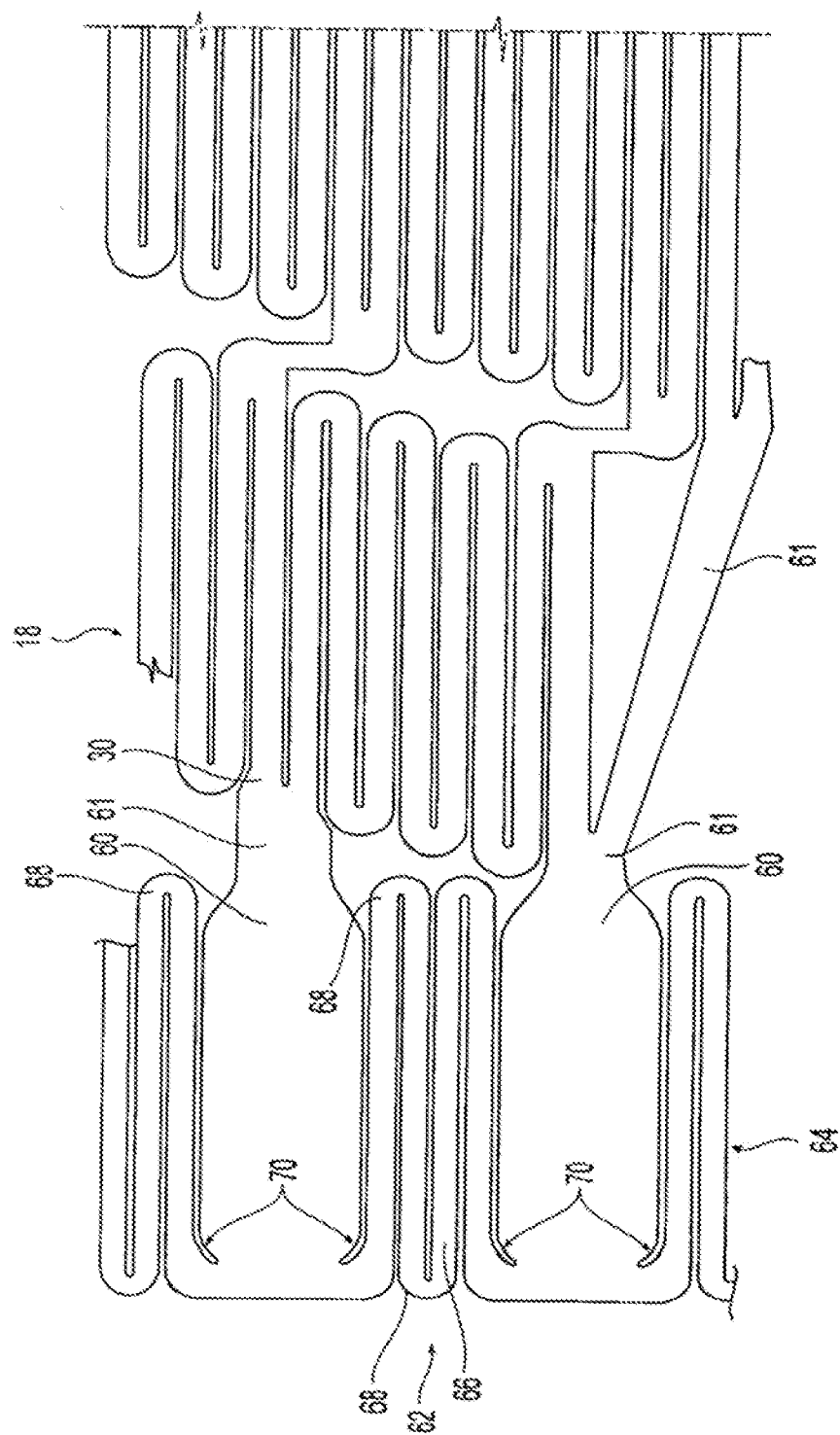

HIGHLY FLEXIBLE STENT AND METHOD OF MANUFACTURE

PRIORITY DATA AND INCORPORATION BY REFERENCE

This application is a continuation-in-part of U.S. application Ser. No. 13/687,874, filed Nov. 28, 2012, which is a division of U.S. patent application Ser. No. 12/526,690, filed as a U.S. national stage application under 35 U.S.C. §371 of International Application No. PCT/US2008/053326, filed on Feb. 7, 2008, now U.S. Pat. No. 8,328,865, which claims the benefit of priority to U.S. Provisional Application No. 60/889,421, filed on Feb. 12, 2007, and is a continuation-in-part of U.S. application Ser. No. 13/970,474, filed Aug. 19, 2013, which is a continuation of U.S. application Ser. No. 11/074,806, filed Mar. 8, 2005, now U.S. Pat. No. 8,512,391, which is a continuation of U.S. patent application Ser. No. 10/231,666, filed Aug. 30, 2002, now U.S. Pat. No. 6,878,162, each of which is incorporated by reference in its entirety into this application. International Application No. PCT/US2007/061917 filed on Feb. 9, 2007 is also incorporated by reference in its entirety into this application.

BACKGROUND

It is known in the medical field to utilize an implantable prosthesis to support a duct or vessel in a mammalian body. One such prosthesis may include a frame-like structure. Such frame-like structures are commonly known as a "stent", "stent-graft" or "covered stent." These structures are referred to collectively herein as a "stent" or an "implantable prosthesis."

The stent or prosthesis can be utilized to support a duct or vessel in the mammalian body that suffers from an abnormal widening (e.g., an aneurysm, vessel contraction or lesion such as a stenosis or occlusion), or an abnormal narrowing (e.g., a stricture). Stents are also utilized widely in the urethra, esophagus, biliary tract, intestines, arteries, veins, as well as peripheral vessels. The stent can be delivered via a small incision on a host body. Hence, the use of stents as a minimally-invasive surgical procedure has become widely accepted.

Previously developed stents for use in the biliary, venous, and arterial systems have been of two broad classes: balloon-expanded and self-expanding. In both of these classes, stents have been made by different techniques, including forming from wire and machining from a hollow tube. Such machining can be done by photo-chemical etching, laser-cutting, stamping, piercing, or other material-removal processes. Other manufacturing techniques have been proposed, such as vacuum or chemical deposition of material or forming a tube of machined flat material, but those "exotic" methods have not been widely commercialized.

One common form of stent is configured as a series of essentially identical rings connected together to form a lattice-like framework that defines a tubular framework. The series of rings may or may not have connecting linkages between the adjacent rings. One example does not utilize any connecting linkages between adjacent rings as it relies upon a direct connection from one ring to the next ring. It is believed that more popular examples utilize connecting linkages between adjacent rings, which can be seen in stent products offered by various companies in the marketplace.

All of the above stent examples utilize a biocompatible metal alloy (e.g., stainless steel, Nitinol or Elgiloy). The most common metal alloy utilized by these examples is Nitinol, which has strong shape memory characteristics so that Nitinol self-expands when placed in the duct or vessel of a mammalian body at normal body temperature. In addition to self-expansion, these stents utilize a series of circular rings placed adjacent to each other to maintain an appropriate longitudinal spacing between each rings. Other examples are shown and described in U.S. Patent Publications 2004/0267353 and 2003/055485, and U.S. Pat. No. 5,824,059. Examples which use a helical configuration are shown and described, to identify a few, in U.S. Pat. Nos. 6,117,165; 6,488,703; 6,042,597; 5,906,639; 6,053,940; 6,013,854; 6,348,065; 6,923,828; 6,059,808; 6,238,409; 6,656,219; 6,053,940; 6,013,854; and 5,800,456.

A need is recognized for a stent that maintains the patency of a vessel with the ability to adapt to the tortuous anatomy of the host by being highly flexible while being loadable into a delivery catheter of sufficiently small profile and easily deliverable to target site in the vessel or duct by having the ability to navigate tortuous ducts or vessels.

DISCLOSURE OF INVENTION

The embodiments described herein relate to various improvements of the structure of an implantable stent that embodies a helical winding. More specifically, the preferred embodiments relate to a stent with a continuous helical winding having interconnected struts joined at vertices, and having bridges connecting sections of the helical winding to each other. At least one end of the stent has an annular ring connected to the helical winding with extensions extending therebetween. At least one extension extends from the annular ring to connect to a bridge and at least one extension extends from the annular ring to connect to a vertex. The struts at the ends of the helical winding also have strut lengths that differ from the strut lengths of the struts in a central portion of the helical winding.

One aspect includes an implantable prosthesis with a continuous helical winding. The winding has a plurality of circumferential sections circumscribing a longitudinal axis from a first end to a second end to define a tube. The circumferential sections are spaced apart along the axis and include a plurality of struts joined together end to end. The end to end joining of two struts of the plurality of struts defines a vertex between the two struts. A plurality of bridges connect one circumferential section to an adjacent circumferential section. An annular ring with a first extension and a second extension extend from the annular ring and connect to the first or second ends of the continuous helical winding. The first extension connects to an end vertex at the first or second end, and the second extension connects to one of the plurality of bridges.

Another aspect includes an implantable prosthesis with a continuous helical winding. The winding has a plurality of circumferential sections circumscribing a longitudinal axis from a first end to a second end to define a tube. The circumferential sections include a first end circumferential section at the first end and a second end circumferential section at the second end and one or more central circumferential sections therebetween. The circumferential sections are spaced apart along the axis and include a plurality of struts joined together end to end. The end to end joining of two struts of the plurality of struts defines a vertex between the two struts. At least one of the vertices of the first or second end circumferential sections is an end vertex, and a plurality of bridges connect one circumferential section to an adjacent circumferential section. An annular ring has a plurality of extensions that extend from the annular ring and connect to the continuous helical winding. At least one extension connects to the end vertex, and at least one of the two struts joined together to define the end vertex has an end strut length. The end strut length is different than a range of central strut lengths of the struts of the one or more central circumferential sections.

These aspects can include the helical winding and the plurality of bridges having an expanded and unimplanted condition. The helical winding can include zig-zag struts, the plurality of bridges can have a minimum width greater than a width of any strut, and the helical winding can have a single helical winding. The helical winding can also have a plurality of separate helical windings connected to each other, at least one of the plurality of bridges can extend substantially parallel with respect to the axis of the implantable prosthesis, and at least one of the plurality of bridges can extend obliquely with respect to an axis extending parallel to the axis of the implantable prosthesis. Furthermore, at least one of the plurality of bridges can directly connect a peak of one circumferential section to another peak of an adjacent circumferential section, at least one of the plurality of bridges can directly connect a peak of one circumferential section to a trough of an adjacent circumferential section, and at least one of the plurality of bridges can directly connect a trough of one circumferential section to a trough of an adjacent circumferential section. Also, a width of at least one strut can be approximately 65 microns, and a width of at least one strut can be approximately 80% of a width of at least one of the plurality of bridges.

Yet another aspect includes a method of manufacturing an implantable prosthesis involving forming a first pattern that defines a continuous helical winding having a plurality of circumferential sections with a first end and a second end. The circumferential sections are spaced apart between the first and second ends and include a plurality of struts joined together end to end. The end to end joining of two struts of the plurality of struts defines a vertex between the two struts, and a plurality of bridges connect one circumferential section to an adjacent circumferential section. The method also involves forming a second pattern that defines an annular ring having a first extension and a second extension extending therefrom and connecting to the first or second ends of the continuous helical winding. The first extension connects to an end vertex at the first or second end, and the second extension connects to one of the plurality of bridges.

Still another aspect includes a method of manufacturing an implantable prosthesis involving forming a first pattern that defines a continuous helical winding having a plurality of circumferential sections with a first end and a second end. The circumferential sections include a first end circumferential section at the first end and a second end circumferential section at the second end and one or more central circumferential sections therebetween. The circumferential sections are spaced apart and include a plurality of struts joined together end to end. The end to end joining of two struts of the plurality of struts defines a vertex between the two struts, and at least one of the vertices of the first or second end circumferential sections is an end vertex. A plurality of bridges connect one circumferential section to an adjacent circumferential section. The method also includes forming a second pattern that defines an annular ring having a plurality of extensions extending therefrom and connecting to the continuous helical winding. At least one extension connects to the end vertex, and at least one of the two struts joined together to define the end vertex has an end strut length. The end strut length is different than a range of central strut lengths of the struts of the one or more central circumferential sections.

These and other embodiments, features and advantages will become apparent to those skilled in the art when taken with reference to the following detailed description in conjunction with the accompanying drawings that are first briefly described.

BRIEF DESCRIPTION OF THE DRAWINGS

The accompanying drawings, which are incorporated herein and constitute part of this specification, illustrate exemplary embodiments of the invention, and, together with the general description given above and the detailed description given below, serve to explain the features of the invention.

FIG. 4 is a close-up side view of a bridge connection of the stent of FIG. 1.

FIG. 5A is a close-up partial side view of an end portion of the stent of FIG. 1.

FIG. 5B is a close-up partial side view of an end portion of the stent of FIG. 1 in an unexpanded configuration.

MODE(S) FOR CARRYING OUT THE INVENTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. Also, as used herein, the terms "patient", "host" and "subject" refer to any human or animal subject and are not intended to limit the systems or methods to human use, although use of the subject invention in a human patient represents a preferred embodiment.

Figure 1:
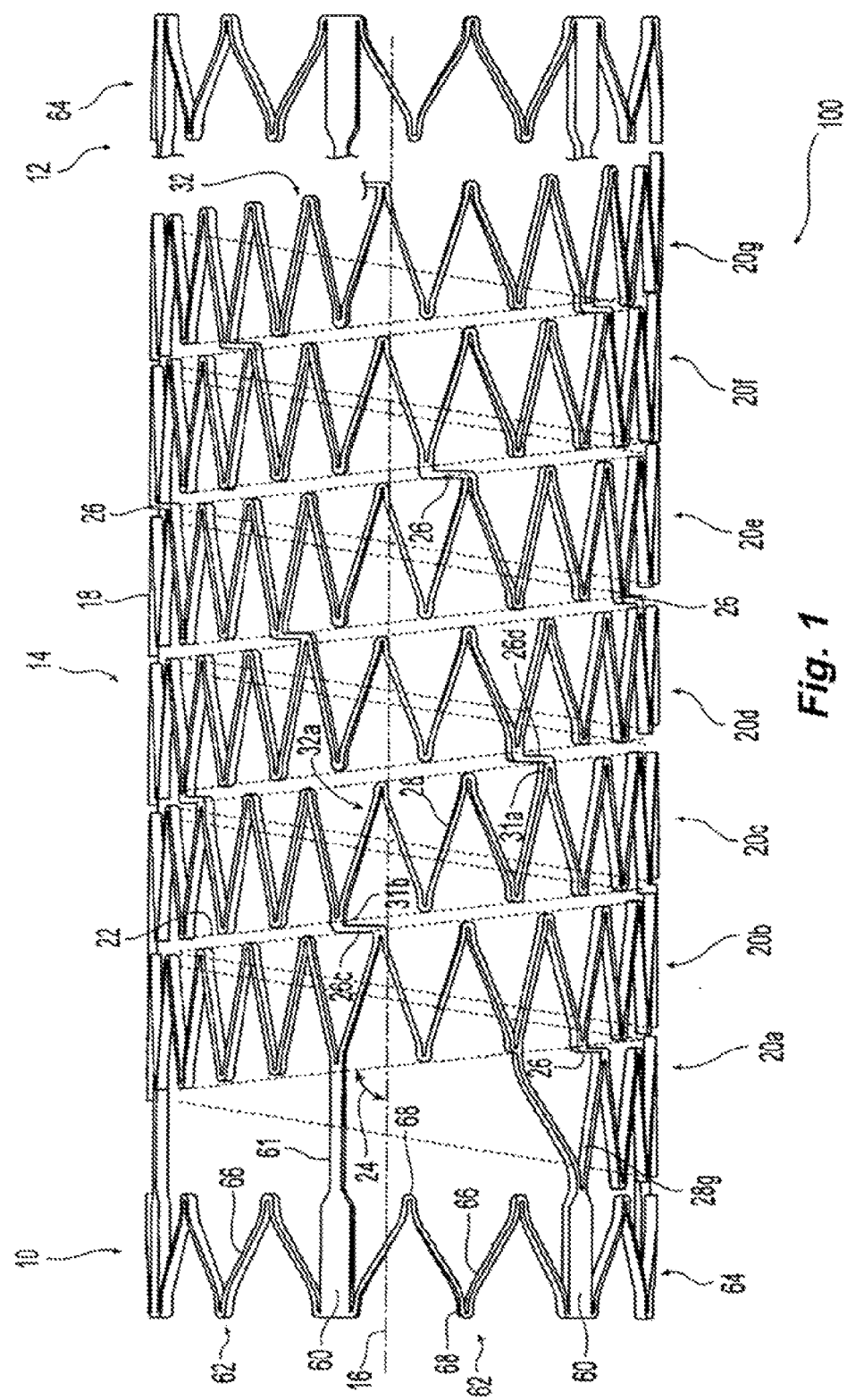
FIG. 1 is a side view of a helical type stent of the preferred embodiment.
Figure 2:
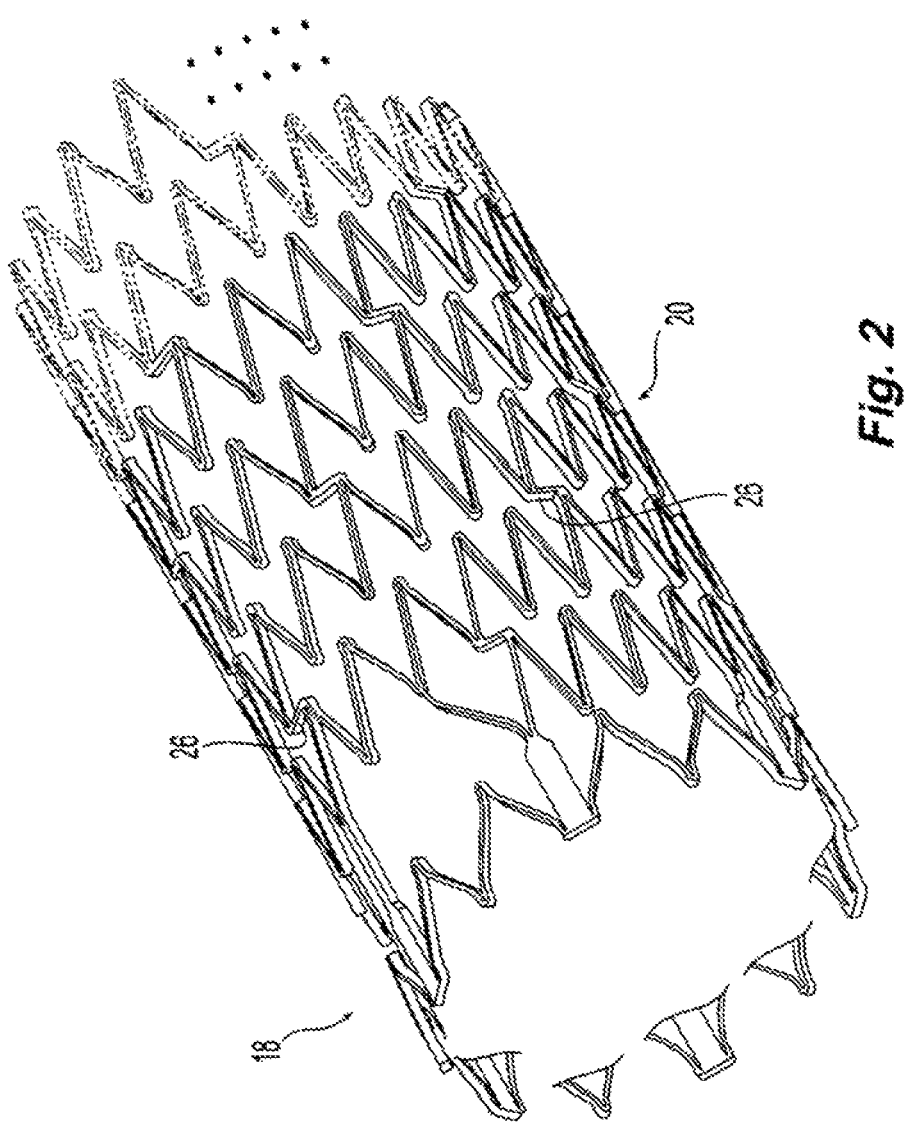
FIG. 2 is a perspective view of a portion of the stent of FIG. 1.

Referring to FIGS. 1 and 2, a stent 100 is shown having a tubular shape and a first end 10, a second end 12, an intermediate portion 14, and a longitudinal axis 16. The intermediate portion 14 includes a continuous helical winding 18. The winding 18 has a plurality of circumferential sections 20 (identified as 20a-20g in FIG. 1) that join together end-to-end and circumscribe the axis 16 from the first end 10 to the second end 12, with the continuation of each circumferential section 20 along the path of the helical winding 18 represented with dashed lines in FIG. 1. In FIGS. 1, 2, 8, and 10-12, the portions of the stent 100 (or stents 200, 300, or 400) in the background of the figure are not shown in detail, for clarity and to clearly show identical features already presented in the foreground of the figure. The circumferential sections 20 are longitudinally spaced apart along the axis 16 and disposed 360 degrees about the axis 16. The axial distances between adjacent circumferential sections 20 define spacing 22, and the spacing 22 is shown in FIG. 1 with the same dashed lines that represent the continuation of the helical winding 18 for each circumferential section 20 in the background of the figure. The spacing 22 of each circumferential section 20 defines a helical angle 24 relative to a plane collinear with the axis 16 (as shown) or relative to an orthogonal plane intersecting the axis 16, with each circumferential section 20 having a helical angle on a first-end facing side and a second-end facing side. Although only one helical winding 18 is illustrated in FIG. 1, more that one helical winding 18 can be employed in the stent 100. For example, a helical winding with a first helical angle can be connected or coupled with another helical winding that has a different second helical angle. Alternatively, the helical winding 18 of FIG. 1 can be utilized as a central portion of the intermediate portion 14 and the helical winding 218 of the stent 200 illustrated in FIG. 8 can be utilized proximate each end of the intermediate portion 14, and vice versa.

The stent 100 includes at least one bridge 26 configured to connect one circumferential section 20 to an axially-spaced adjacent circumferential section 20. The bridge 26 extends generally circumferentially around the axis 16 on a generally orthogonal plane with respect to the axis 16. That is, the bridge 26 forms a circumferential connector or bridge member (i.e., "circumferential bridge") between circumferential sections 20 of the helical winding 18. Preferably, there are a plurality of bridges 26 interconnecting the circumferential sections 20 to adjacent circumferential sections 20.

Figure 3A:
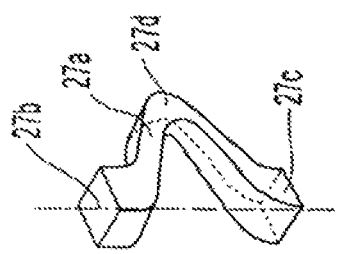
FIG. 3A is a close-up, perspective view of an alternate embodiment of a bridge connection illustrated in FIG. 3.
Figure 3:
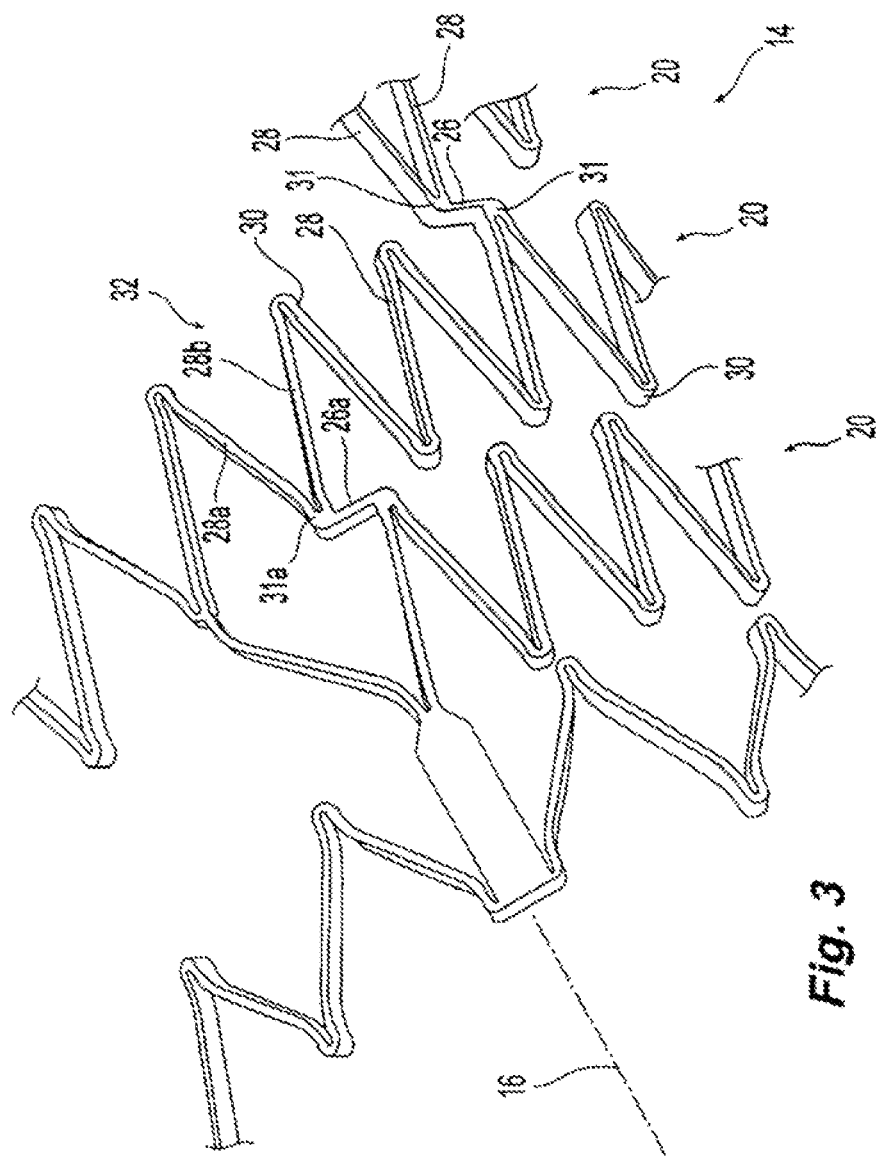
FIG. 3 is a close-up, perspective view of the stent of FIG. 2.

As illustrated in FIG. 3, in the intermediate portion 14, each circumferential section 20 includes a plurality of struts 28 joined together by strut vertices 30 and bridge vertices 31 disposed at ends of the struts 28. The strut vertices 30 connect two struts 28 together, and the bridge vertices 31 connect one or two struts 28 and a bridge 26 together. The bridge vertices 31 are larger than the strut vertices 30 in order to accommodate the connection of the bridges 26 to the struts 28. The bridges 26 connect the bridge vertices 31 in one circumferential section 20 to the bridge vertices 31 in an adjacent circumferential section 20. The bridges 26 provide a circumferential offset, equal to the length of the bridge 26, between connected bridge vertices 31 that approximately face each other across the spacing 22 between adjacent circumferential sections 20. Upon expansion of the stent 100, the bridges 26 maintain an offset orientation between the bridge vertices 31, so that the strut vertices 30 and bridge vertices 31 of one circumferential section 20 do not abut or near the opposing strut vertices 30 or bridge vertices 31 of an adjacent circumferential section 20. Also, when the stent 100 is bent slightly and forced to conform to a curve, the strut vertices 30 and bridge vertices 31 disposed on the inside path of the curve will move towards each other and close the spacing 22 between adjacent circumferential sections 20 (and possibly continue moving towards each other so that one circumferential section 20 moves into the path of the helical winding 18 occupied in part by another circumferential section 20), but avoid or minimize direct contact or interference because the bridges 26 cause the strut vertices 30 and bridge vertices 31 of one circumferential section 20 to interdigitate with those of another circumferential section 20. This interdigitation of the circumferential sections 20 allows the stent 100 to bend easily without interference between struts 28, strut vertices 30, and bridge vertices 31 on adjacent circumferential sections 20 of the helical winding 18. That is, each of the bridges 26 is configured so that the end of the bridge 26 connected to one bridge vertex 31 is circumferentially aligned with the other end of the bridge 26 connected to another bridge vertex 31 on a plane that is orthogonal to the axis 16, whether the stent 100 is in an expanded or unexpanded configuration. As illustrated in FIG. 3A, an alternative bridge 27a can be non-linear, but one end of the bridge 27b remains circumferentially aligned with the other end of the bridge 27c (illustrated by a dashed line between bridge ends 27b and 27c) in a plane orthogonal to the axis 16. As such, the bridge 26 is not required to be linear as illustrated herein but can include curved, zig-zag, meandering curves, sinusoidal, or curvilinear configurations as long as the end points connecting to opposing bridge vertices 31 are aligned with the circumference of a tube defined by the stent 100. Alternatively, as illustrated in FIG. 3A, the bridges 26 of the various embodiments can also provide an extension 27d that permits comparatively slight extension of the stent 100 in the direction of the axis 16 or beyond the radial periphery of the stent 100 defined by the expansion of the circumferential sections 20, as described and shown in U.S. Publication No. 2006/0060266; U.S. Pat. No. 7,763,067; U.S. Publication No. 2006/0074480; U.S. Pat. No. 7,780,721; and U.S. Publication No. 2006/0064155, all of which are incorporated by reference herein in their entirety.

While providing these aforementioned advantages, the circumferential bridges 26 provide for a more generally even expansion of the stent 100 because some of the bridges 26 are disposed away from the expanding portions of the circumferential sections 20 that define the helical winding 18. As illustrated in FIG. 3, in the preferred embodiments, the circumferential sections 20 have undulations that are formed by the generally linear struts 28 coupled together at the strut vertices 30 or bridge vertices 31, which are deformed during expansion and compression of the stent 100. Where the bridge 26a is coupled to struts 28a and 28b in FIG. 3, the bridge vertex 31a is sufficiently rigid so that it isolates any deformation of the struts 28a and 28b (during expansion of the stent 100, for example) from the bridge 26a, so that bridge 26a is not or only minimally deformed. Preferably, the stent 100 is a Nitinol self-expanding stent of approximately 6 mm final diameter, and the bridge 26 is approximately 100 microns wide in the direction of the axis 16, approximately 200 microns thick in the radial direction from the axis 16, and approximately 130 microns long in the circumferential direction between the bridge vertices 31. The bridge vertices 31, illustrated in FIG. 4, are approximately 90 microns wide in the direction of axis 16, approximately 200 microns thick in the radial direction from the axis 16, and approximately 1500 microns long in the circumferential direction around axis 16. Other materials can be used instead of Nitinol, such as, for example, weak shape memory metals (e.g., stainless steel, platinum, Elgiloy), shape memory polymers, bioresorbable metals and polymers.

Figure 8:
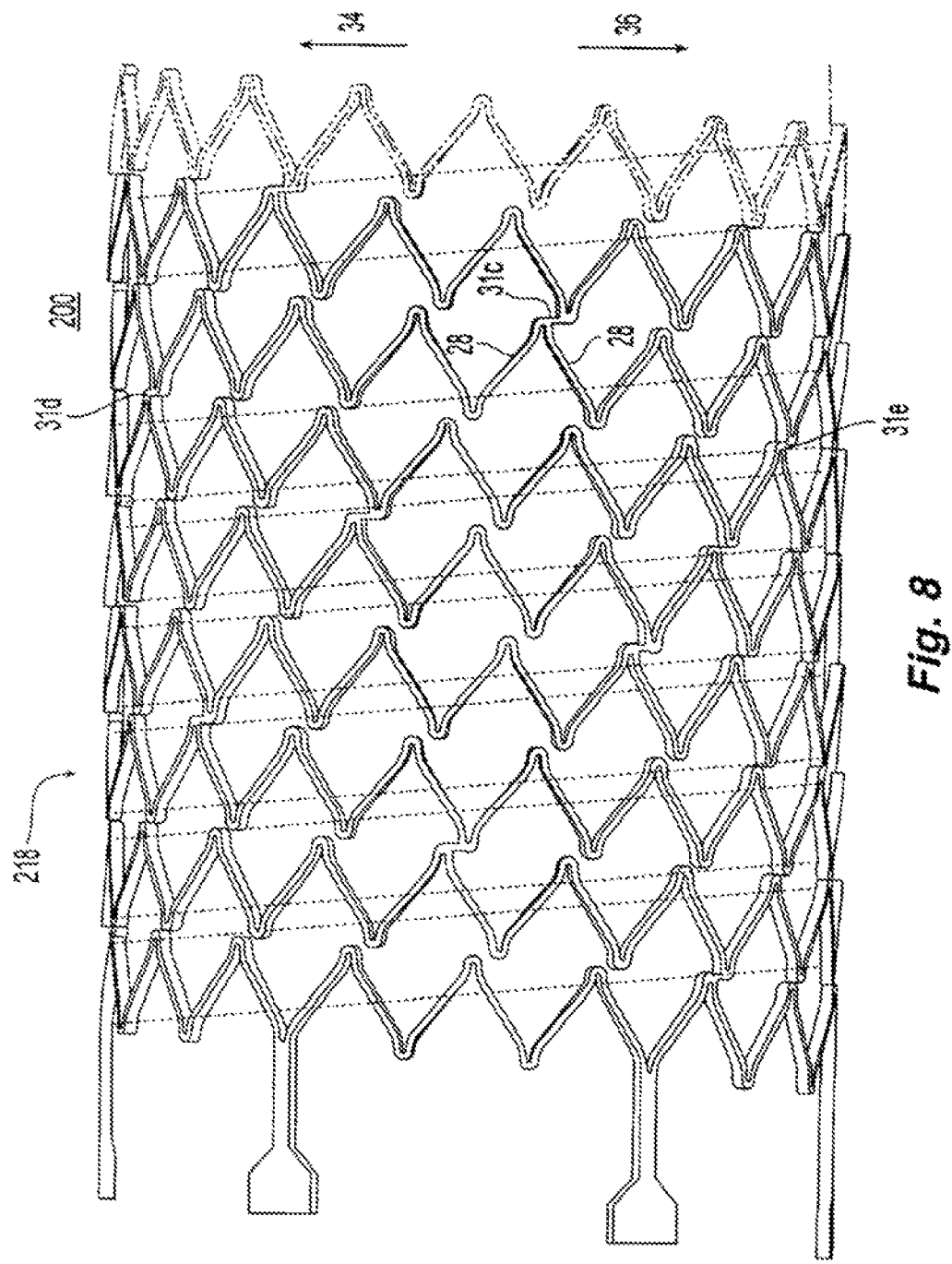
FIG. 8 is a side view of a portion of an alternative stent to the stent of FIG. 1.

Referring to FIGS. 1 and 2, it is noted that the number of bridges 26 and struts 28 can be varied. In one embodiment, the number of struts 28 above and below any bridges 26 (within a single arcuate undulation section 32) can be the same. An arcuate undulation section 32 is a series of struts 28 and strut vertices 30 extending between two bridge vertices 31 on a single circumferential section 20. For example, with reference to circumferential section 20c in FIG. 1, bridge vertices 31a and 31b have five struts 28 therebetween (which define five undulations in the arcuate undulation section 32a). Bridges 26c and 26d join the arcuate undulation section 32a to arcuate undulation sections 32 in adjacent circumferential sections 20b and 20d, respectively, which are spaced at a predetermined distance (spacing 22) from circumferential section 20c. In particular, five struts 28 are disposed along any one of the arcuate undulation sections 32 between any one bridge 26 and another next bridge 26 in the intermediate portion 14, in a circumferential direction that is either clockwise or counterclockwise around the axis 16. It is believed that a design having equal number struts 28 provides advantageous characteristics with regard to flexibility and strength. In the preferred embodiments, the number of struts 28 in the clockwise or counterclockwise circumferential directions can range from three to nine, inclusive. Alternatively, the number of struts 28 in one circumferential direction can be different from the number of struts 28 in the other circumferential direction. For example, as illustrated in FIG. 8, there are seven struts 28 disposed between bridge vertex 31c and bridge vertex 31d in the circumferential counterclockwise direction identified by arrow 34 and five struts 28 disposed between bridge vertex 31c and bridge vertex 31e in the circumferential clockwise direction identified by arrow 36. In the preferred embodiments, a pattern of three struts 28 in the counter-clockwise direction and five struts 28 in the clockwise direction from a single bridge vertex 31 (a three-five pattern), a five-five pattern, or a five-seven pattern are utilized.

Figure 7:
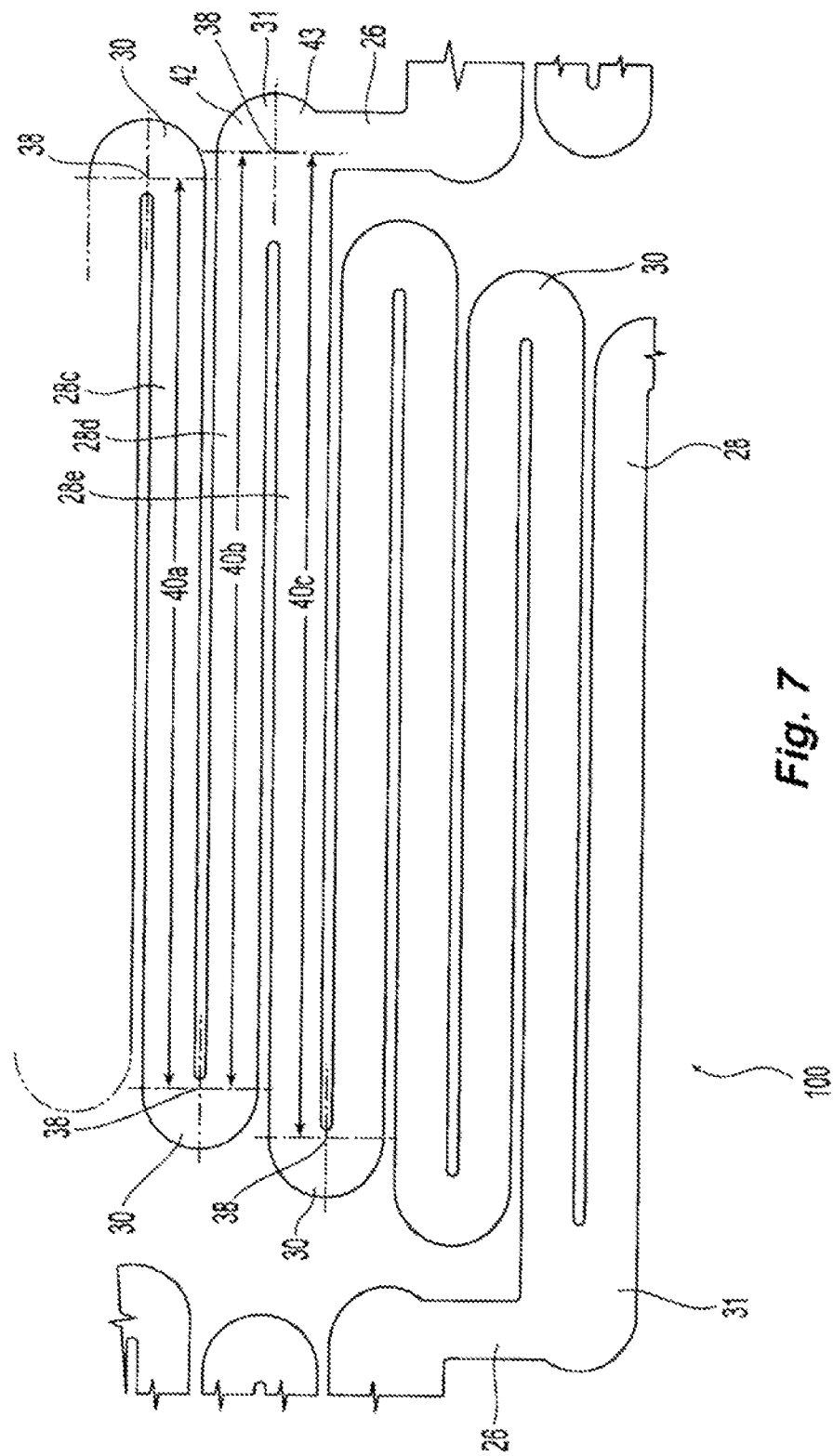
FIG. 7 is a close-up partial side view of an embodiment of the stent in an unexpanded configuration.

With reference to FIG. 7, a portion of the stent 100 is shown in a compressed and unimplanted configuration. In order to discuss the various features of the struts 28 and bridges 26, the following definition of strut length is used. A "strut length" is the length of a strut 28 from a center 38 of a radius of curvature of one end of the strut 28 (at a strut vertex 30 or bridge vertex 31) to another center 38 of a radius of curvature located on the other end of the strut 28 (at a strut vertex 30 or bridge vertex 31). As such, as illustrated in FIG. 7, the strut length of the strut 28c (extending between two strut vertices 30) is strut length 40a, the strut length of the strut 28d (extending between a strut vertex 30 and a portion 42 of a bridge vertex 31) is strut length 40b, and the strut length of strut 28e (extending between a strut vertex 30 and a portion 43 of a bridge vertex 31) is strut length 40c. Portion 43 is disposed more closely to the bridge 26 than portion 42. Using this definition, it can be seen that strut length 40c is greater than strut length 40b, and that strut length 40b is greater than strut length 40a. In an alternative embodiment, the strut lengths of sequential struts 28 in a circumferential section 20 can alternate between a relatively short strut 28 and a relatively long strut 28 to allow for the axial advancement of the helical winding 18.

Figure 10:
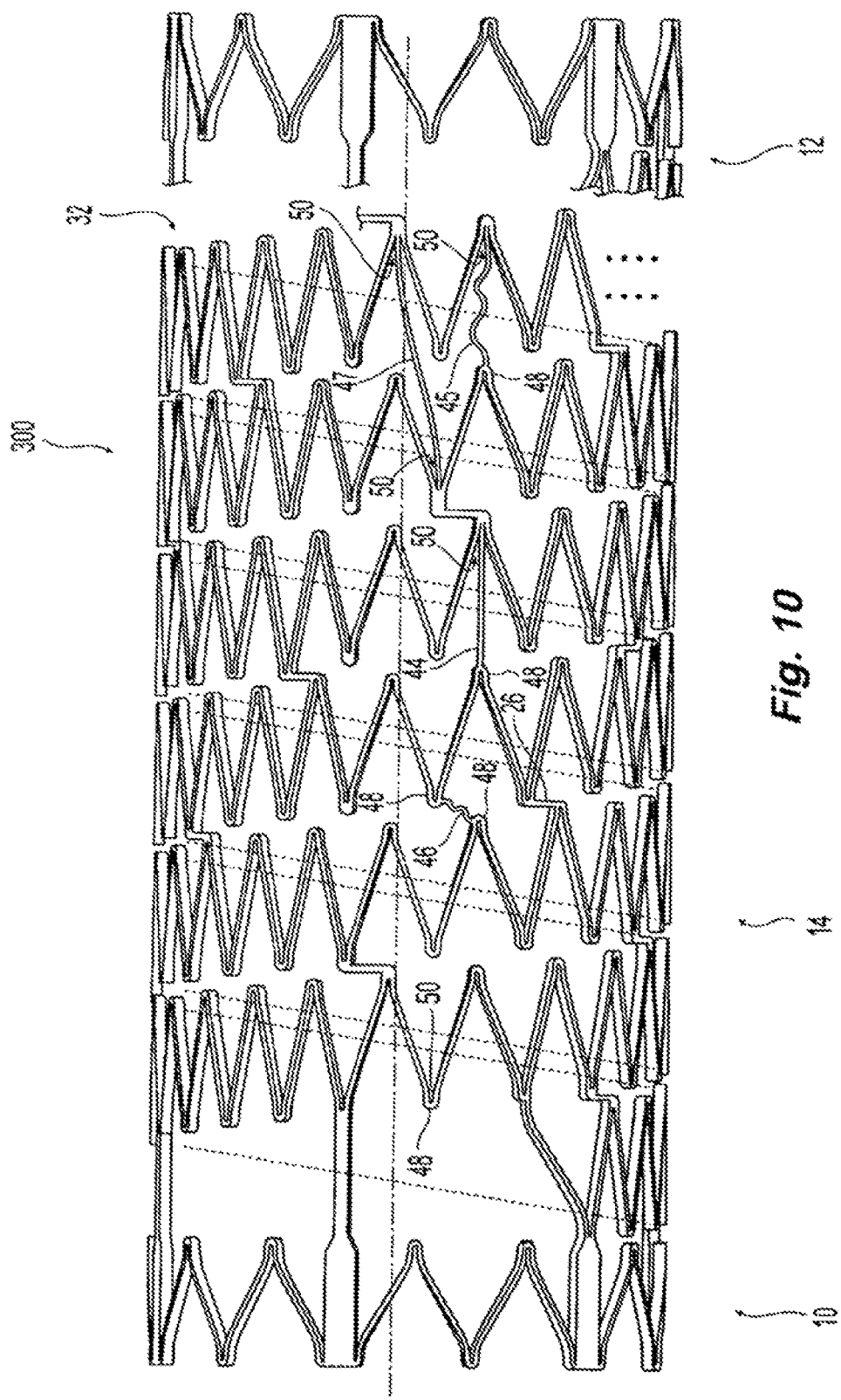
FIG. 10 is a side view of a portion of another alternative stent to the stent of FIG. 1.

Further, the use of bridges 26 to connect adjacent circumferential sections 20 is not limited to the configuration illustrated in the figures but can include other configurations where the bridge 26 is on a plane obliquely intersecting the axis 16 or generally parallel to the axis 16. For example, as shown in FIG. 10, an alternative stent 300 includes an axial bridge 44 extending substantially parallel with respect to the axis 16 of the stent. Also illustrated is a wave type spring bridge 45 (e.g., curvilinear in profile), an oblique bridge 46 extending obliquely with respect to an axis extending parallel to the axis 16, and a long bridge 47 extending far enough between bridge vertices 31 so that there is a "bypassed" strut vertex 30 or another bridge vertex passed by and not engaged with the long bridge 47. As also illustrated in FIG. 10, the stent 300 can utilize a combination of bridge types. Alternatively, the bridges 26, 44, 45, 46, or 47 can directly connect a peak 48 of one circumferential section 20 to another peak 48 of an adjacent circumferential section, as illustrated by oblique bridge 46. In yet another alternative, the bridges 26, 44, 45, 46, or 47 can connect a peak 48 to a trough 50 of an adjacent circumferential section 20, as illustrated by axial bridge 44 and wave type spring bridge 45. In a further alternative, the bridges 26, 44, 45, 46, or 47 can connect a trough 50 to a trough 50, as illustrated by long bridge 47. Moreover, the undulations of the arcuate undulation section 32 can be wave-like in pattern. The wave-like pattern can also be generally sinusoidal in that the pattern can have the general form of a sine wave, whether or not such wave can be defined by a mathematical function. Alternatively, any wave-like form can be employed so long as it has amplitude and displacement. For example, a square wave, saw tooth wave, or any applicable wave-like pattern defined by the struts where the struts have substantially equal lengths or unequal lengths. Also the stents 100, 200, 300, or 400 can be stents that are bare, coated, covered, encapsulated, bioresorbable or any portion of such stents.

It is appreciated that the struts 28 and circumferential sections 20 in the intermediate portion 14 of the stent 100 are supported directly or indirectly on both axial sides (the sides facing spacing 22) by bridges 26 because they fall between other adjacent circumferential sections 20. However, the axially endmost turns of the helical winding 18 (the axially endmost circumferential sections 20, such as circumferential section 20a in FIG. 1) are supported by bridges 26 only on the side of the circumferential section 20 facing another circumferential section 20, and these endmost circumferential sections 20 lack bridges 26 on the sides that do not face an adjacent circumferential section 20, which can affect the proper and even orientation of the struts 28 in these endmost circumferential sections 20 during the contraction or expansion of the stent 100. Any distortions attributable to this one-sided bridge 26 arrangement are small and are usually negligible. However, when markers are attached to the endmost turns of the winding 18 (the endmost circumferential sections 20) with extensions, the lengths of the markers and the extensions are believed to amplify any distortion of the endmost turns. This unevenness is particularly noticeable in a helical winding because the struts are generally of unequal length in order to provide a square-cut end to the stent, and any small distortions of the endmost turns are amplified to differing degrees by the different lengths of marker extensions.

There are several effects of the marker movement referred to above. Cosmetically, the stent can be given a non-uniform appearance that is objectionable to a clinician. If the distortions are large enough, there can be interference between or overlapping of the markers. These distortions can arise during manufacture of the stent, when the pre-form of a self-expanded stent is expanded to its final size. Similar distortions can arise when a finished stent is compressed for insertion into a delivery system, or when a stent is in place in vivo but held in a partially-compressed shape by the anatomy.

Referring to FIGS. 1-3 and particularly 5A-5B, at the first end 10 and second end 12 of the stent 100 there are provided markers 60 extending from the strut vertices 30 of the helical winding 18 with extensions 61. Reinforcing or connecting structures 62 are formed in the stent pre-form (i.e., in the initial manufacturing state of the stent 100) and stabilize the shape and orientation of markers 60 during the expansion of the stent 100 and during the manufacture of the stent 100. It is believed that these connecting structures 62 serve the additional function of improving the stability of the markers 60 when the stent 100 is collapsed for the purpose of delivering the stent to a location within a living body. Further, these connecting structures 62 are also believed to improve the stability of the stent 100 in vivo by improving the resistance to deformation of the markers 60.

With the use of the connecting structures 62, the distortions at the ends 10 and 12 of the stent 100 can be reduced or mostly eliminated. Specifically, the connecting structure 62 is formed by an annular ring 64 that includes a series of end struts 66 and bending segments 68 (similar to the struts 28 and strut and bridge vertices 30 and 31) and is connected between adjacent markers 60 in order to present reactive forces to resist distortion from the expansion and compression of the struts 28. Because these end struts 66 are connected at an axially outer end of the markers 60, they present the greatest possible leverage to maintain the longitudinal axial alignment of the markers 60 and extensions 61 while presenting radial compressive and expansion forces similar to those of the struts 28. These end struts 66 are cut into the stent pre-form at the same time that the strut 28 and bridge 26 pattern of the stent 100 is cut, typically using a laser cutting apparatus or by a suitable forming technique (e.g., etching or EDM). These end struts 66 (along with bending segments 68) then tend to hold the markers 60 and the extensions 61 in parallel or generally in longitudinal axial alignment with the axis 16 when the stent pre-form is expanded during the manufacturing process.

Once the stent pre-form has been expanded, the end struts 66 can be either removed or left in place to form part of the finished stent 100. If it is desired to remove the end struts 66, then the end struts 66 can be designed with sacrificial points, i.e., there can be notches or other weakening features in the body of the end struts 66 where the end struts 66 attach to the markers 60, so that the end struts 66 can be easily removed from the stent 100 by cutting or breaking the end struts 66 at the sacrificial points.

Alternatively, the end struts 66 can be designed so that they remain part of the stent 100. In this case, there would be no artificially weakened sacrificial point at the connection to the markers 60. After the stent pre-form is expanded, the final manufacturing operations would be completed, including cleaning, heat-treating, deburring, polishing, and final cleaning or coating. The resulting stent can then have the end struts 66 in place as an integral part of the stent 100 structure.

In the preferred embodiment, shown in FIGS. 5A and 5B, the markers 60 are approximately 620 microns wide in the circumferential direction and approximately 1200 microns long in the direction of axis 16. Most preferably, the markers 60 are unitary with the extension 61 of the helical winding 18, are generally rectangular in configuration, and can have the inside surface of each marker 60 curved to conform to the tubular form of the stent 100.

Alternatively, the markers 60 can be formed as spoon-shaped markers joined to the extensions 61 by welding, bonding, soldering or swaging to portions or ends of the extensions 61. In a further alternative, materials can be removed from either the luminal or abluminal surface of the markers 60 to provide a void, and a radiopaque material can be joined to or filled into the void. The markers 60 can be mounted at the end of extensions 61. The end struts 66 joining the markers 60 can be approximately 80 microns wide in the circumferential direction and approximately 1500 microns long in the direction of the axis 16 when the stent 100 is in a compressed state, as illustrated in FIG. 5B. In the embodiment illustrated in FIGS. 5A and 5B, there are four end struts 66 between two adjacent markers 60. In the preferred embodiments, the rectangular marker 60 can have its length extending generally parallel to the axis 16 and its circumferential width being greater than two times the width of any strut 28 (i.e., circumferential width in the compressed configuration). In one embodiment, the circumferential width of at least one strut 28 is approximately 6S microns and the circumferential width of the at least one strut 28 is approximately 80-95% of a width of the bridge 26 in the direction of the axis 16.

Referring to FIG. 5B, the structure of the end struts 66 that connect to the markers 60 are preferably provided with a slight curvature 70 (and corresponding curvature on the markers 60) to provide for strain relief as the end struts 66 are expanded.

In an alternative embodiment, the connecting structure 62 includes two end struts 66 (instead of the four of the preferred embodiment) of approximately 90 microns wide in the circumferential direction (when the stent 100 is in the compressed configuration) and approximately 2000 microns long in the direction of the axis 16. It should be noted that four end struts 66 can be utilized when, for example, no marker 60 is used or only a minimal number of markers 60 are needed. The markers 60 in the embodiments are preferably approximately 620 microns wide in the circumferential direction and approximately 1200 microns long in the direction of the axis 16. The markers 60 are preferably mounted on the extensions 61 that are approximately 200 microns wide in the circumferential direction and approximately 2000 microns long in the direction of the axis 16. Preferably, the stent 100, in the form of a bare stent, is manufactured from Nitinol tubing approximately 200 microns thick and having an approximate 1730 micron outside diameter, and is preferably designed to have an approximately 6 mm finished, expanded, and unimplanted outside diameter.

There are several features of the stent 100 that are believed to be heretofore unavailable in the art. Consequently, the state of the art is advanced by virtue of these features, which are discussed below.

First, as noted previously, the continuous helical winding 18 can have a plurality of circumferential sections 20. A plurality of bridges 26 extend on a plane generally orthogonal with respect to the axis 16 to connect the circumferential sections 20. By this configuration of the circumferential bridges 26 for the helical winding 18, a more uniform expansion of the stent 100 is achieved.

Second, each of the circumferential sections 20 can be configured as arcuate undulation sections 32 (FIGS. 1 and 2) disposed about the axis 16. The arcuate undulation sections 32 can have bridges 26 with struts 28 connected thereto so that the struts 28 connecting to the bridges 26 have a length greater than a length of other struts 28 that are not connected directly to the bridges 26. With reference to FIG. 7, it is noted that the struts 28 can have a strut length 40c that is greater than a strut length 40b, and a strut length 40b that is greater than a strut length 40a.

Figure 6:
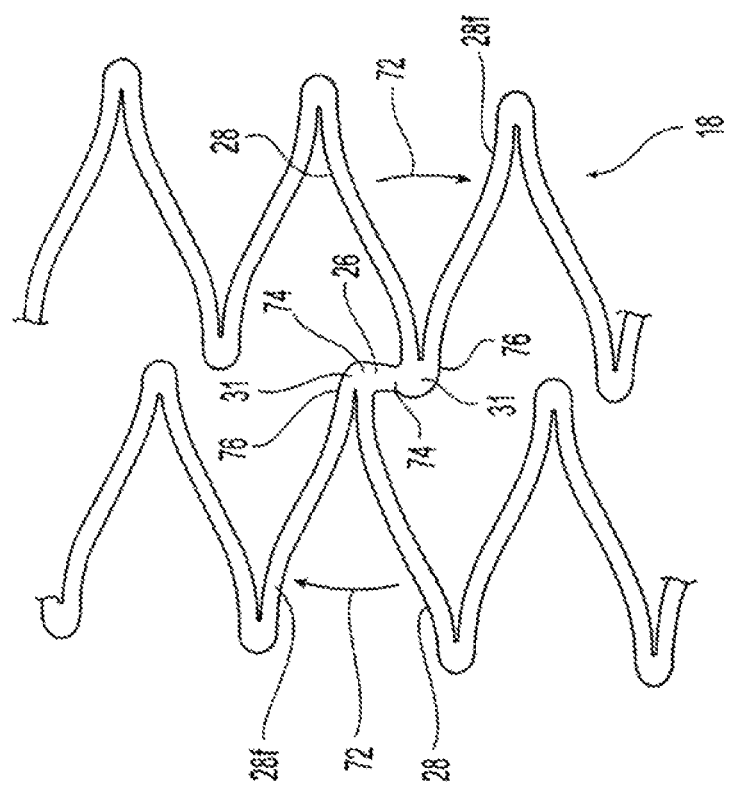
FIG. 6 is a close-up partial side view illustrating the loading forces and distortion of an alternative embodiment of the bridge connection.

Third, the bridge 26 can be connected to the adjacent arcuate undulation section 32 at respective locations other than the peaks 48 of the adjacent arcuate undulation section 32. For example, as shown in FIG. 4, the bridge 26 has an axial width selected so that the edges of the bridge 26 form an offset 71 that sets the bridge 26 slightly back from the outermost edge 31f of the bridge vertices 31. By virtue of such arrangement, distortion is believed to be reduced in the struts 28, and substantially reduced at the struts 28 connecting directly to the bridge vertices 31. Specifically, FIG. 6 illustrates the increased bending strains placed on the stressed struts 28f when the bridge 26 is stressed by bending or by torsion of the stent 100. In the example illustrated in FIG. 6, a clockwise force is applied in the direction of the arrows 72 which results from the bending or torsion of the stent 100, and the greatest stresses are believed to be developed at high-stress points 76 where the stressed struts 28f connect to the bridge vertices 31. It is believed that distortion of the strut pattern can be expected to result in increased local strains, which can cause small regions of the strut pattern to experience higher than normal strains. It is also believed that such increased strains can lead to premature failure in vivo. Because the high-stress points 76 in the preferred embodiments are located away from the bridge 26 by a distance corresponding to the circumferential width of the bridge vertex 31, as illustrated in FIG. 6, localized strains at the bridge 26 connecting points 74 (where the bridge 26 connects to the bridge vertices 31) are less than those experienced at the high-stress points 76. In addition, the struts 28 can have linear segments, curved segments or a combination of curved and linear segments. Also, by virtue of the circumferential bridges 26, the struts 28 can have a curved configuration between peaks 48 of a winding 18 as illustrated, for example, in FIG. 6.

Fourth, in the embodiment where a bridge 26 extends on a plane generally orthogonal with respect to the axis 16, there is at least one annular ring 64 connected to one of the first and second ends 10 and 12 of the continuous helical winding 18. The annular ring 64 is believed to reduce distortions to the markers 60 proximate the end or ends of the helical winding 18.

Figure 9:
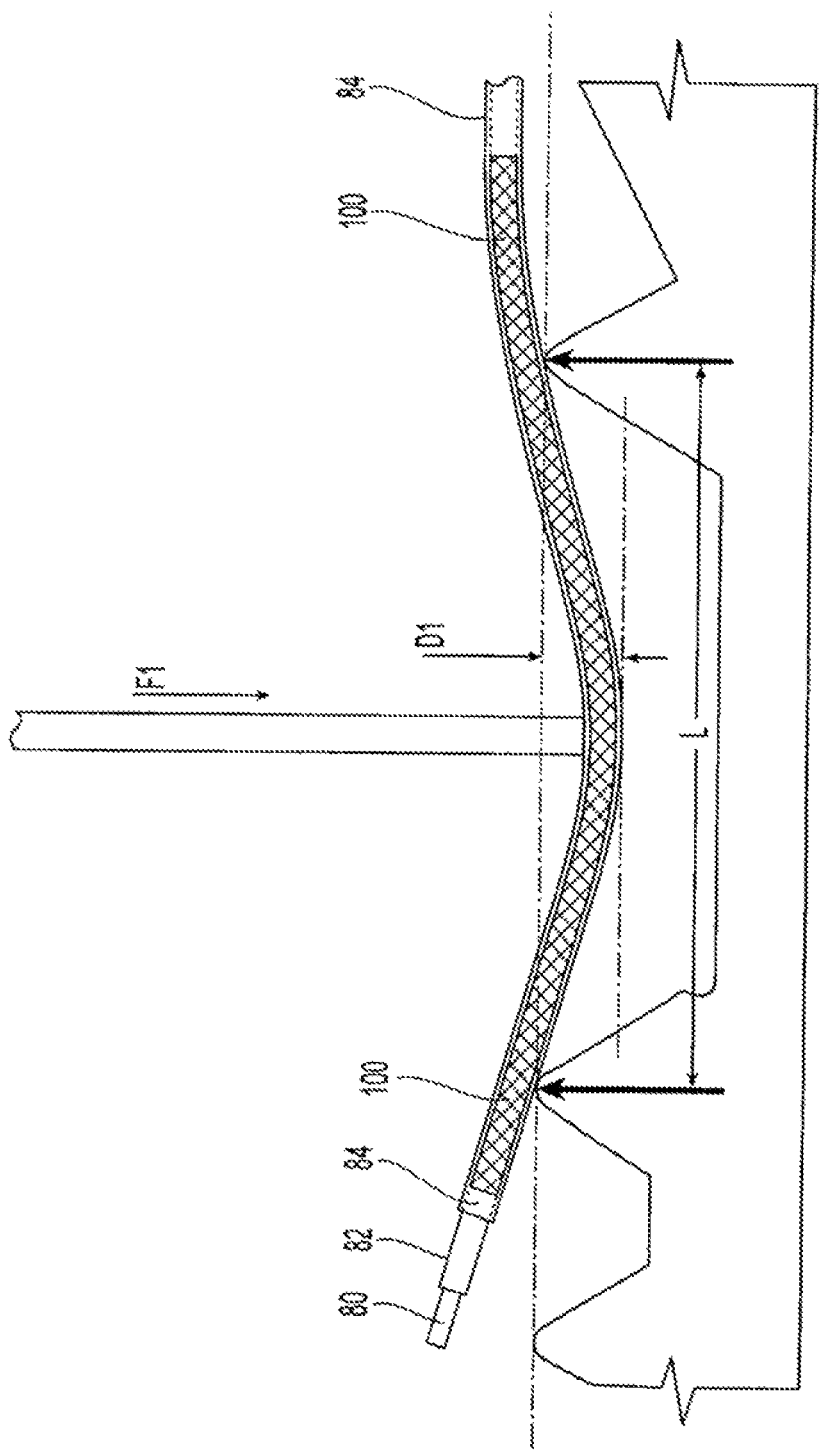
FIG. 9 illustrates a testing stand to determine flexibility of the preferred stent in a delivery catheter.

Fifth, in the preferred embodiment, where the stent 100 includes a continuous helical winding 18 and a plurality of circumferential sections 20 defining a tube having an axial length of about 60 millimeters and an outer diameter of about 6 millimeters, at least one bridge 26 is configured to connect two circumferential sections 20 together so that the force required to displace a portion of the stent 100 between two fixed points located about 30 millimeters apart is less than 3.2 Newton for a displacement of about 3 millimeters along an axis orthogonal to the axis 16 of the stent 100. In particular, as illustrated in FIG. 9, the stent 100 is loaded in carrier sheaths 80 made of PEBAX, where the stent 100 is supported by an inner catheter 82 and outer catheter 84. The outer catheter 84 has an inner diameter of about 1.6 millimeters. Both the inner and outer catheters 82 and 84 are commercially available 6 French catheters under the trade name Luminexx® III manufactured by Angiomed GmbH & Co., Medizintechnik KG of Germany, and available from C.R. Bard, Inc. of Murray Hill, N.J. The two catheters 82 and 84 with the stent 100 in between are placed on a 3-point bending jig where the outer catheter 84 is supported at two locations spaced apart at distance L of about 30 millimeters. A load F1 is placed on the stent 100 proximate the center of the distance L and the force required to bend the catheters 82 and 84 and the stent 100 over a displacement D1 of about 3 millimeters is measured. For the stent 100 of the preferred embodiment illustrated in FIG. 1, the force required to achieve a displacement D1 of 3 millimeters is less than 3.2 Newtons. As compared with a known helical stent (sold under the trade name Lifestent®) and having an outer diameter of approximately 6 millimeters and a length of about 40 millimeters), using the same testing configuration, the force required to displace the known stent in a Luminexx® III catheter sheath over a distance D1 of approximately 3 millimeters is approximately 3.2 Newtons or greater. It is believed that the lower the force required to displace the stent (when contained in catheters 82 and 84) a distance D1 (of about 3 millimeters), the better the ability of the stent and the catheters to navigate tortuous anatomy. By requiring less than 3.2 Newtons force in this test, the preferred embodiment stent 100 is believed to be highly flexible during delivery and implantation, as compared to known stents and delivery systems, and this high flexibility facilitates the ability of the clinician to navigate a duct or vessel necessary to deliver and implant the stent. In the particular embodiment tested, the force F1 for stent 100 was approximately 1.7 Newtons for a 6 French Luminexx® III catheter.

Sixth, by virtue of the structures described herein, an advantageous technique to load a helical stent 100 is provided that does not have physical interference between arcuate undulation sections 32 and bridges 26 in the compressed configuration of the stent 100 in a generally tubular sheath from an inside diameter of approximately 6 millimeters to the compressed stent 100 configuration of approximately 2 millimeters (6 French). Specifically, where a stent is utilized with approximately 48 arcuate undulation sections 32 (which include the struts 28) in each circumferential section 20, and 9 bridges 26 for connection to adjacent circumferential sections 20, it has been advantageously determined that the stent 100 does not require a transition portion and a tubular end zone, as is known in the art. In particular, the method can be achieved by utilization of a physical embodiment of the stent 100 (e.g., FIGS. 1-5) and compressing the stent 100. The stent 100 has an outside diameter of approximately 6 millimeters that must be compressed to fit within the generally tubular sheath 80 that has an outside diameter of approximately 2 millimeters (6 French) and an inside diameter of approximately 1.6 millimeters, without any of the struts 28 of the stent 100 crossing each other when compressed and inserted into the sheath 80. In other words, in the expanded unimplanted configuration of the stent 100, none of the struts 28 and bridges 26 physically interfere with, i.e., overlap or cross, other struts 28 or bridges 26 of the stent 100. The stent 100 can be compressed, without the use of transition strut segments (or the use of the annular rings 64) at the axial ends of the helical winding 18, to a smaller outer diameter of about 3 millimeters or less (and preferably less than 2 millimeters) where the inner surfaces of the struts 28 and bridges 26 remain substantially contiguous without physical interference of one strut 28 with another strut 28 or with a bridge 26.

Figure 14:
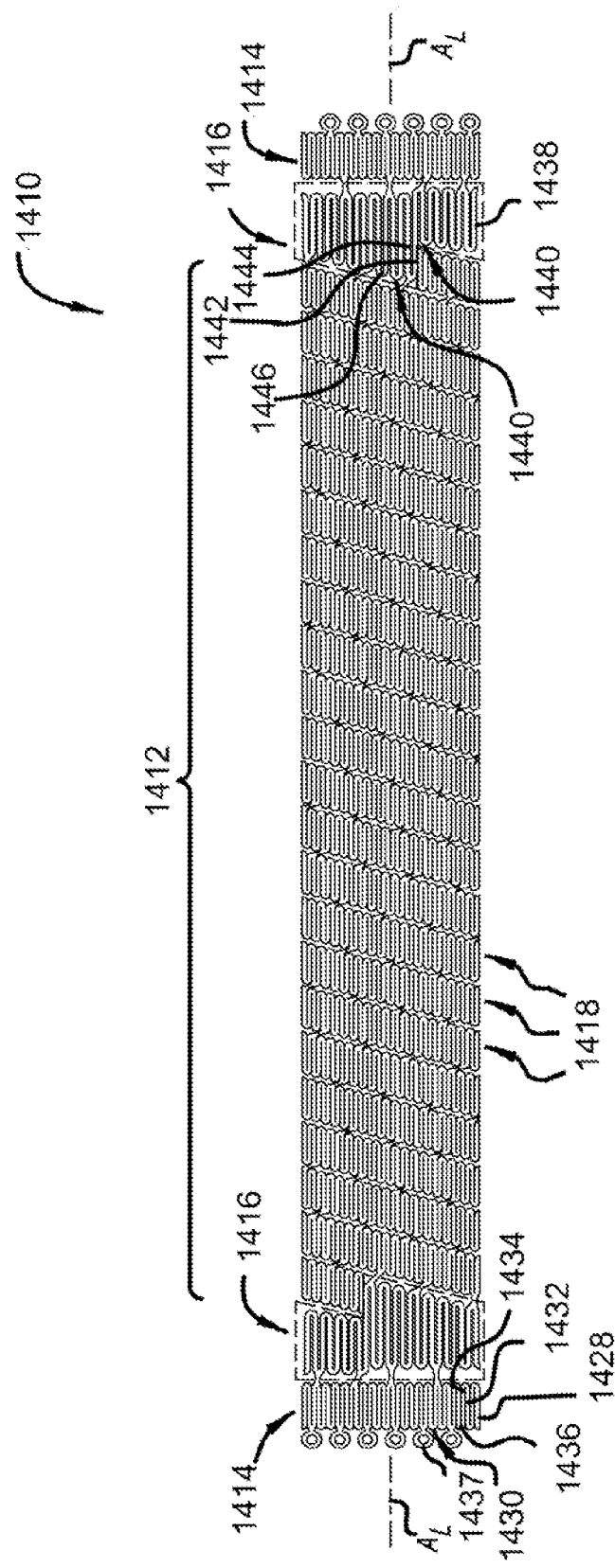
FIG. 14 is a broken flattened view of a helical stent according to the invention in an unexpanded state, wherein the stent has been cut parallel to its longitudinal axis and laid flat.

Turning now to FIG. 14, a helical stent 1410 according to the invention is shown. The stent has a collapsed configuration with a first smaller diameter for insertion into a body vessel, and self-expands to an expanded or deployed configuration with a second larger diameter for deployment within the vessel. The stent is preferably a laser-cut tubular construction of a superelastic metal alloy such as nickel-titanium.

Figure 15:
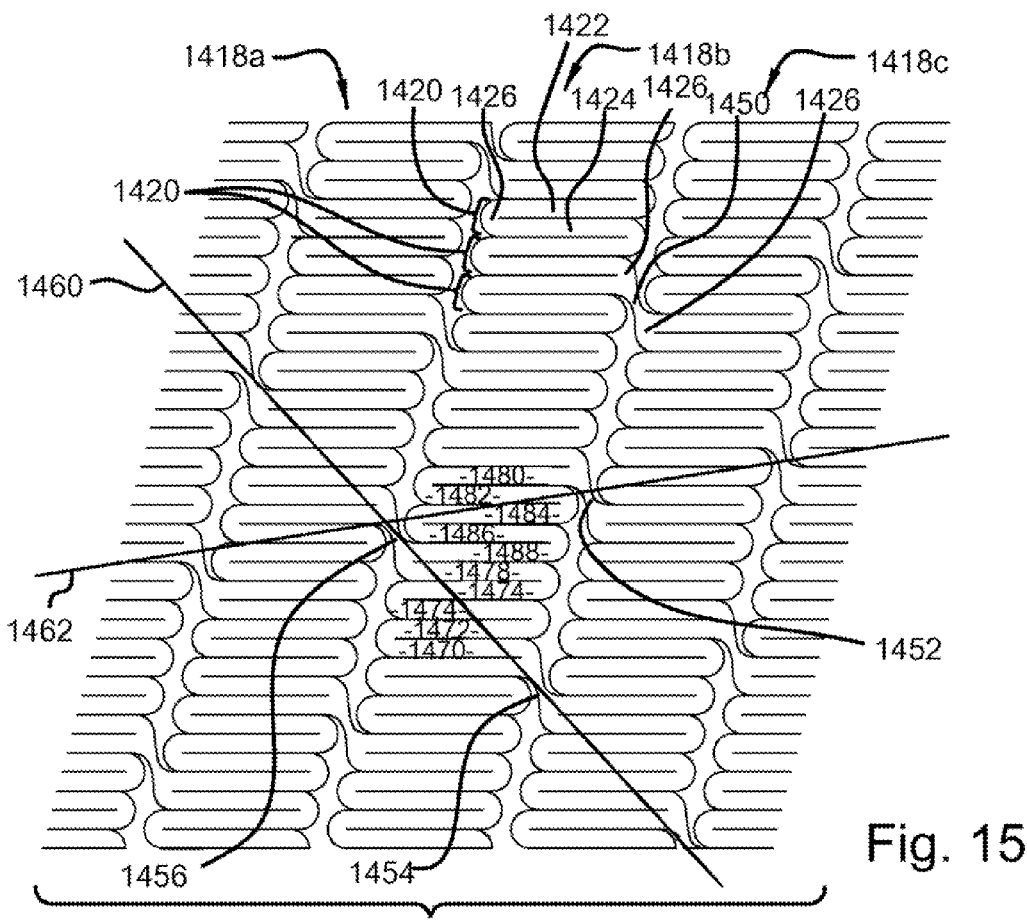
FIG. 15 is an enlarged broken flattened view of a central portion of the helical stent of FIG. 14.

The stent 1410 includes a central portion 1412, a cylindrical portion 1414 at each end of the stent 1410, and a transition zone 1416 between the central portion 1412 and each cylindrical end portion 1414. The central portion 1412 is comprised of a plurality of helical circumferential windings (single turns of a helix) 18 of substantially like undulations (in length and width) 1420, with each undulation 1420 being defined by two adjacent struts, e.g., struts 1422, 1424, and a loop 1426 connecting the struts (FIG. 15). The cylindrical end portion 1414 is comprised of preferably a single cylindrical winding 1428 of like undulations 1430, with each such undulation 1430 being defined by two adjacent struts, e.g., struts 1432, 1434, and a loop 1436 connecting the struts. Optionally, one or more structures 1437 adapted to receive or otherwise be coupled to radiopaque markers (not shown) can be provided at the ends of one or more of the undulations 1430. The transition zone 1416 is comprised of preferably a single winding 1438 of undulations 1440 that preferably progressively increase in size, with each such undulation 1440 being defined by two adjacent struts, e.g., struts 1442, 1444, and a loop 1446 connecting the struts.

In each of sections 1412, 1414 and 1416, the undulations 1420, 1430, 1440 extend in a generally longitudinal direction. That is, when the stent is in a collapsed configuration, as shown in FIG. 14, struts of the helical portion (e.g., 1422 and 1424), cylindrical portion (e.g., 1432 and 1434) and transition zone (e.g., 1442 and 1444) all extend substantially parallel to the longitudinal axis of the stent. In the expanded configuration, adjacent struts are moved apart and angled relative to each other.

Referring to FIG. 15, particularly with respect to the central portion 1412, as the windings 1418a, 1418b, 1418c are longitudinally displaced along the length of the stent, bridges, e.g. 1450, 1452, 1454 and 1456, are provided to connect together the loops 1426 of undulations 1420 on adjacent windings, e.g. 1418a and 1418b, and 1418b and 1418c, to prevent stent unwinding. The bridges 1450, 1452, 1454, 1456 can be seen to be arranged in right-handed and left-handed helical "strings" (right-handed string 1460 and left-handed string 1462) which extend about the stent.

An exemplar central portion 1412 of the stent 1410 is now described. Referring to FIG. 15, the central portion 1412 of the stent 1410 includes repeating undulations 1420 (each comprising two struts 1422, 1424 and a loop 1426) that are helically wound in circumferential windings 1418a, 1418b, 1418c, etc. There are preferably nineteen undulations 1420 in each circumferential winding 1418a, 1418b, 1418c and the undulations are interdigitated. With reference to windings 1418b and 1418c, a bridge 1450, 1452, 1454 is located every five undulations therebetween, and each bridge joins loops of undulations on the adjacent windings 1418a, 1418b which are one and one-half pitches away (or two struts over from directly across) in the "short" direction. That is, all bridges in the central portion 1412 of the stent preferably extend in the same direction, longitudinally crosswise across the helical space. This preferred exemplar embodiment provides a very symmetrical distribution of bridges. In particular, traveling from any one bridge, e.g. bridge 1454, to the next bridge, e.g. bridge 1456, along the right-hand string 1460 of bridges, traverses exactly two and one half undulations (or five struts 1470, 1472, 1474, 1476 and 1478). Moreover, traveling from any one bridge, e.g. bridge 1452, to the next bridge, e.g. bridge 1456, along the left-handed string 1462 of bridges, also traverses exactly two and one half undulations (or five struts 1480, 1482, 1484, 1486 and 1488). This design gives very even torsional flexibility and expandability, and the stent may be twisted considerably in either direction without buckling.

Figure 16:
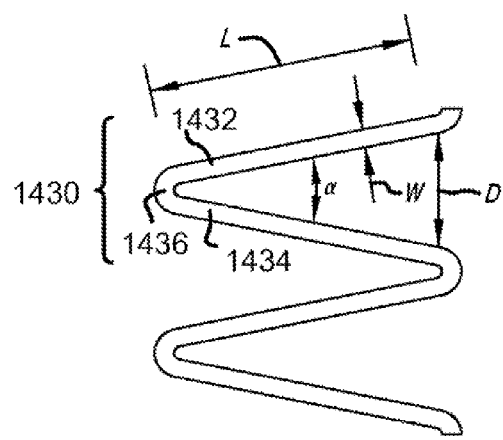
FIG. 16 is an enlarged broken flattened view of a transition zone portion of the helical stent of FIG. 14.

Referring now to FIG. 16, the transition zone 1416 of the stent 1410 is shown. The transition zone, as stated above, includes struts that progressively increase in length. The long transition zone struts 1490, 1492 are relatively wider (in the cylindrical plane) than the shorter transition zone struts 1494, 1496 to compensate for the greater bending moments imposed by the longer struts. Moreover, even the shortest transition zone strut 1498 is preferably longer and wider than the struts 1422, 1424 of the central portion 1412.

Figure 17:
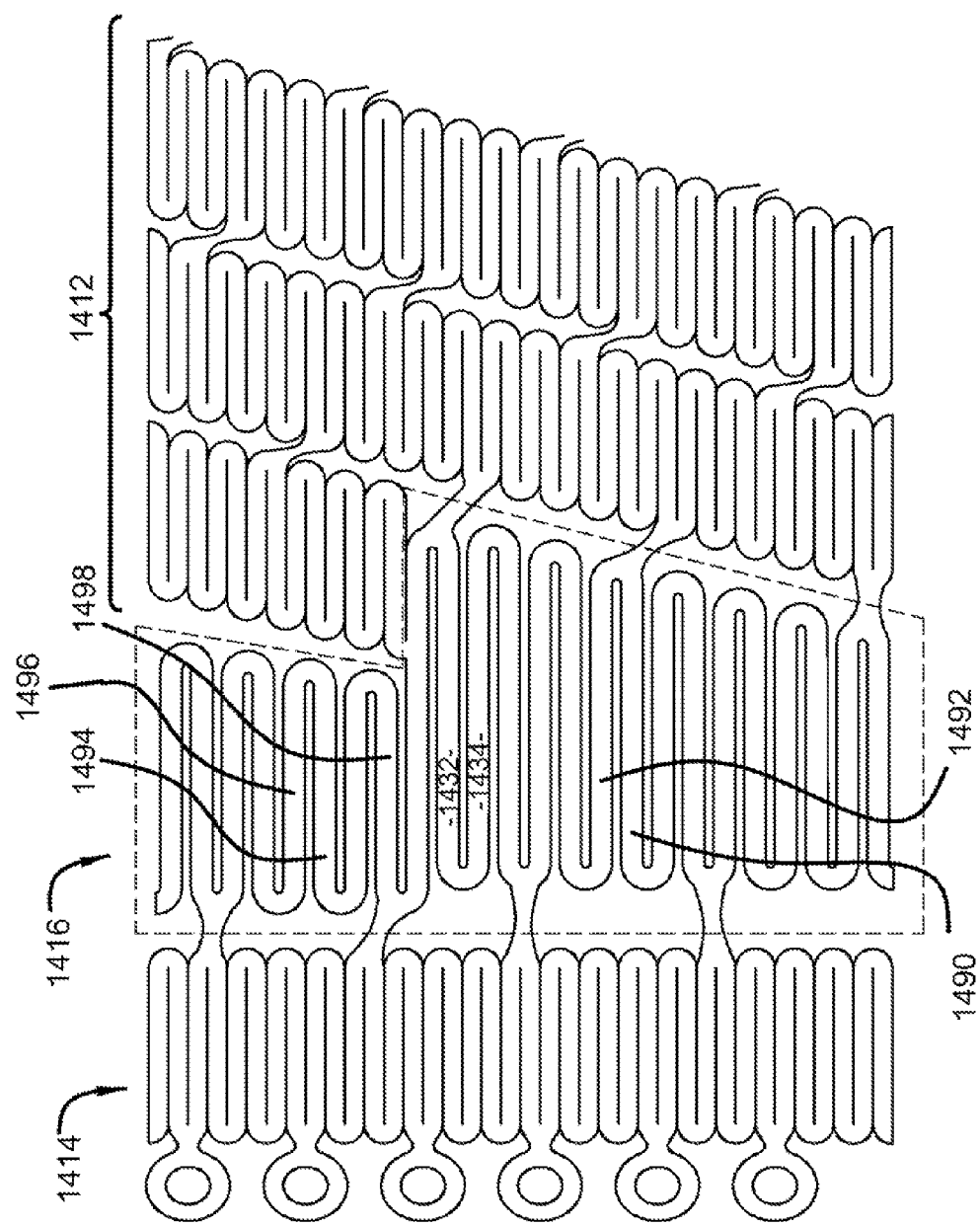
FIG. 17 is a schematic view of a plurality of struts of the transition zone of FIG. 16 shown in an open configuration.

More particularly, referring to FIGS. 16 and 17, for substantially uniform expansion of the stent, it is desirable for the opening distance D (i.e., the distance between the ends of two adjacent struts, e.g. struts 1432 and 1434, when the stent is in an open configuration) to be approximately even throughout the transition zone 16. Accordingly, the opening angle a between pairs of longer struts in the transition zone, e.g. struts 1432 and 1434, must be smaller than the opening angle $\alpha$ between shorter struts, e.g. struts 1494 and 1496. In addition, the bending stiffness of the longer struts must be even greater than in proportion to their increased bending moment.

Bio-active agents can be added to the stent (e.g., either by a coating or via a carrier medium such as resorbable polymers) for delivery to the host vessel or duct. The bioactive agents can also be used to coat the entire stent. A coating can include one or more non-genetic therapeutic agents, genetic materials and cells and combinations thereof as well as other polymeric coatings.

Non-genetic therapeutic agents include anti-thrombogenic agents such as heparin, heparin derivatives, urokinase, and PPack (dextrophenylalanine proline arginine chloromethylketone); anti-proliferative agents such as enoxaprin, angiopeptin, or monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, and mesalamine; antineoplastic/antiproliferative/anti-miotic agents such as paclitaxel, 5-fluorouracil, cisplatin, vinblastine, vincristine, epothilones, endostatin, angiostatin and thymidine kinase inhibitors; anesthetic agents such as lidocaine bupivacaine; and ropivacaine; anti-coagulants, an RGD peptide-containing compound, heparin, antithrombin compounds, platelet receptor antagonists, anti-thrombin antibodies, anti-platelet receptor antibodies, aspirin, prostaglandin inhibitors, platelet inhibitors and tick anti-platelet peptides; vascular cell growth promotors such as growth factor inhibitors, growth factor receptor antagonists, transcriptional activators, and translational promotors;

vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; and agents which interfere with endogenous vascoactive mechanisms.

Genetic materials include anti-sense DNA and RNA, DNA coding for, anti-sense RNA, tRNA or rRNA to replace defective or deficient endogenous molecules, angiogenic factors including growth factors such as acidic and basic fibroblast growth factors, vascular endothelial growth factor, epidermal growth factor, transforming growth factor alpha and beta, platelet-derived endothelial growth factor, platelet-derived growth factor, tumor necrosis factor alpha, hepatocyte growth factor and insulin like growth factor, cell cycle inhibitors including CD inhibitors, thymidine kinase ("TK") and other agents useful for interfering with cell proliferation the family of bone morphogenic proteins ("BMPs"), BMP-2, BMP-3, BMP-4, BMP-5, BMP-6 (Vgr-1), BMP-7 (OP-1), BMP-8, BMP-9, BMP-10, BMP-1, BMP-12, BMP-13, BMP-14, BMP-15, and BMP-16. Desirable BMP's are any of BMP-2, BMP-3, BMP-4, BMP-5, BMP-6 and BMP-7. These dimeric proteins can be provided as homodimers, heterodimers, or combinations thereof alone or together with other molecules. Alternatively or, in addition, molecules capable of inducing an upstream or downstream effect of a BMP can be provided. Such molecules include any of the "hedgehog" proteins, or the DNAs encoding them.

Cells can be of human origin (autologous or allogeneic) or from an animal source (xenogeneic), genetically engineered if desired to deliver proteins of interest at the deployment site. The cells can be provided in a delivery media. The delivery media can be formulated as needed to maintain cell function and viability.

Suitable polymer coating materials include polycarboxylic acids, cellulosic polymers, including cellulose acetate and cellulose nitrate, gelatin, polyvinylpyrrolidone, cross-linked polyvinylpyrrolidone, polyanhydrides including maleic anhydride polymers, polyamides, polyvinyl alcohols, copolymers of vinyl monomers such as EVA, polyvinyl ethers, polyvinyl aromatics, polyethylene oxides, glycosaminoglycans, polysaccharides, polyesters including polyethylene terephthalate, polyacrylamides, polyethers, polyether sulfone, polycarbonate, polyalkylenes including polypropylene, polyethylene and high molecular weight polyethylene, halogenated polyalkylenes including polytetrafluoroethylene, polyurethanes, polyorthoesters, proteins, polypeptides, silicones, siloxane polymers, polylactic acid, polyglycolic acid, polycaprolactone, polyhydroxybutyrate valerate and blends and copolymers thereof, coatings from polymer dispersions such as polyurethane dispersions (for example, BAYHDROL® fibrin, collagen and derivatives thereof, polysaccharides such as celluloses, starches, dextrans, alginates and derivatives, hyaluronic acid, squalene emulsions. Polyacrylic acid, available as HYDROPLUS® (from Boston Scientific Corporation of Natick, Mass.), and described in U.S. Pat. No. 5,091,205, the disclosure of which is hereby incorporated herein by reference, is particularly desirable. Even more desirable is a copolymer of poly lactic acid and polycaprolactone.

The preferred stents can also be used as the framework for a vascular graft. Suitable coverings include nylon, collagen, PTFE and expanded PTFE, polyethylene terephthalate, KEVLAR® polyaramid, and ultra-high molecular weight polyethylene. More generally, any known graft material can be used including synthetic polymers such as polyethylene, polypropylene, polyurethane, polyglycolic acid, polyesters, polyamides, their mixtures, blends and copolymers.

In the preferred embodiments, some or all of the bridges 26 can be bio-resorbed while leaving the undulating strut 28 configuration essentially unchanged. In other embodiments, however, the entire stent 100 can be resorbed in stages by a suitable coating over the resorbable material. For example, the bridges 26 can resorb within a short time period after implantation, such as, for example, 30 days. The remaining helical stent framework (made of a resorbable material such as metal or polymers) can thereafter resorb in a subsequent time period, such as, for example, 90 days to 2 years from implantation.

Markers 60 can be provided for all of the embodiments described herein. The marker 60 can be formed from the same material as the stent 100 as long as the material is radiographic or radiopaque. The marker material can also be formed from gold, tantalum, platinum for example. The marker 60 can be formed from a marker material different from the material used to form another marker 60.

The stents described herein can be, with appropriate modifications, delivered to an implantation site in a host with the delivery devices described and shown in U.S. Patent Publication Nos. 2005/0090890 or 2002/0183826, U.S. Pat. No. 6,939,352 or 6,866,669.

Although the preferred embodiments have been described in relation to a frame work that define a tube using wire like members, other variations are within the scope of the invention. For example, the frame work can define different tubular sections with different outer diameters, the frame work can define a tubular section coupled to a conic section, the frame work can define a single cone, and the wire-like members can be in cross-sections other than circular such as, for example, rectangular, square, or polygonal.

Even though various aspects of the preferred embodiments have been described as self-expanding Nitinol stents suitable for use in the common bile duct or superficial femoral artery, it should be apparent to a person skilled in the art that these improvements can be applied to self-expanding stents of all sizes and made from any suitable material. Further, such stents can be applied to any body lumen where it is desired to place a structure to maintain patency, prevent occlusive disease, or for other medical purposes, such as to hold embolization devices in place. Further, the features described in the embodiments can be applied to balloon-expanded stents made from malleable or formable materials and intended to be expanded inside a suitable body lumen. The features described in the embodiments can also be applied to bare metal stents, stents made from other than metallic materials, stents with or without coatings intended for such purposes as dispensing a medicament or preventing disease processes, and stents where some or all of the components (e.g., struts, bridges, paddles) of the stents are biodegradable or bioresorbable.

The embodiments use the example of a 6 mm self-expanding stent, but can be applied with equal merit to other kinds of stents and stents of other sizes. Specifically, stents for use in peripheral arteries are customarily made in outer diameters ranging from 3 mm to 12 mm, and in lengths from 10 mm to 200 mm. Stents of larger and smaller diameters and lengths can also be made accordingly. Also, stents embodying the features of the embodiments can be used in other arteries, veins, the biliary system, esophagus, trachea, and other body lumens.

In the embodiment illustrated in FIG. 1, the stent 100 includes the first end 10, the second end 12, and the intermediate portion 14, each surrounding the axis 16. The intermediate portion 14 includes the helical winding 18, and the first end 10 and second end 12 each include the annular ring 64. As illustrated in FIG. 1, the helical winding 18 of the stent 100 is disposed at an angle (the helical angle 24) to the axis 16, i.e., a plane defined by the struts 28 of the winding 18 is at a non-orthogonal angle to the axis 16. As also illustrated in FIG. 1, the annular rings 64 of the stent 100 are orthogonal to the axis 16, i.e., a plane defined by the end struts 66 of the annular ring 64 is orthogonal to the axis 16. These differing geometries (helical and orthogonal) of the helical winding 18 and the annular rings 64 are connected together by the extensions 61, which extend between the winding 18 and annular ring 64, or by direct connection without an extension 61 where the winding 18 and annular ring 64 are disposed proximate to each other, as illustrated in FIG. 1 at the last strut 28g. The last strut 28g is the final strut 28 in the series of struts 28 of the helical winding 18, and there is a last strut 28g proximate the first end 10 and a last strut 28g proximate the second end 12.

Figure 11:
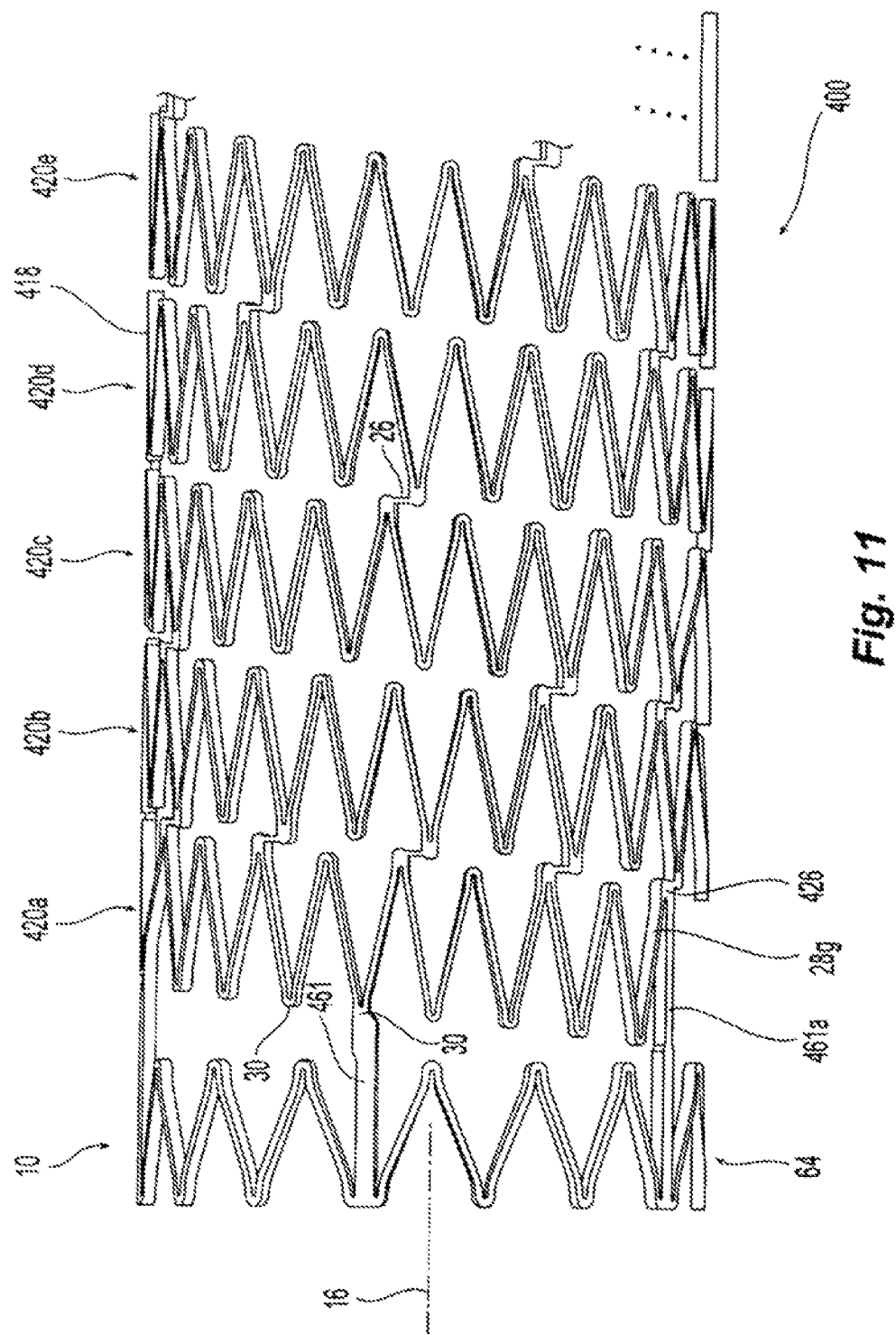
FIG. 11 is a side view of an end of a helical type stent of another preferred embodiment.
Figure 12:
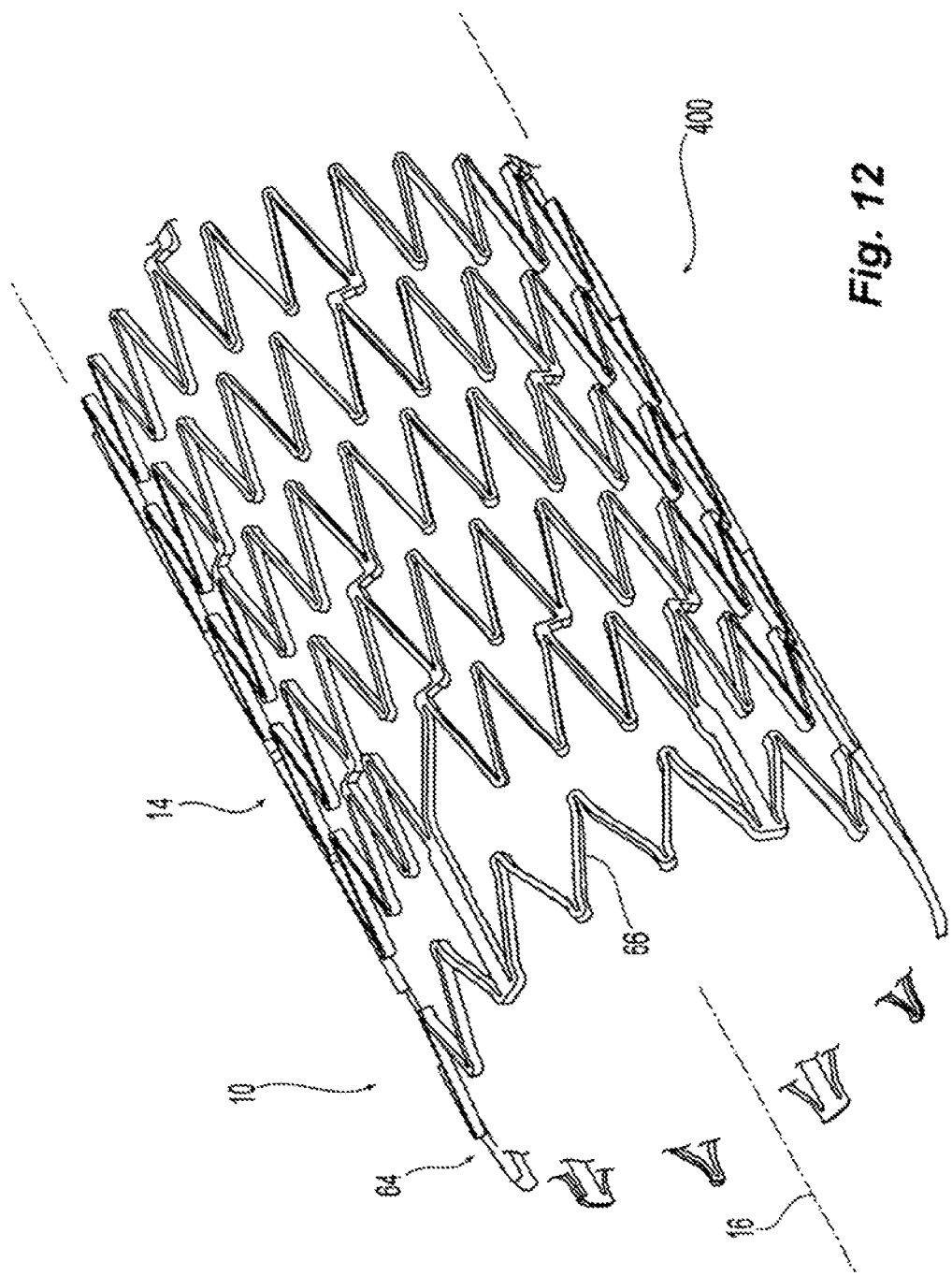
FIG. 12 is a perspective view of the end of the stent of FIG. 11.
Figure 13:
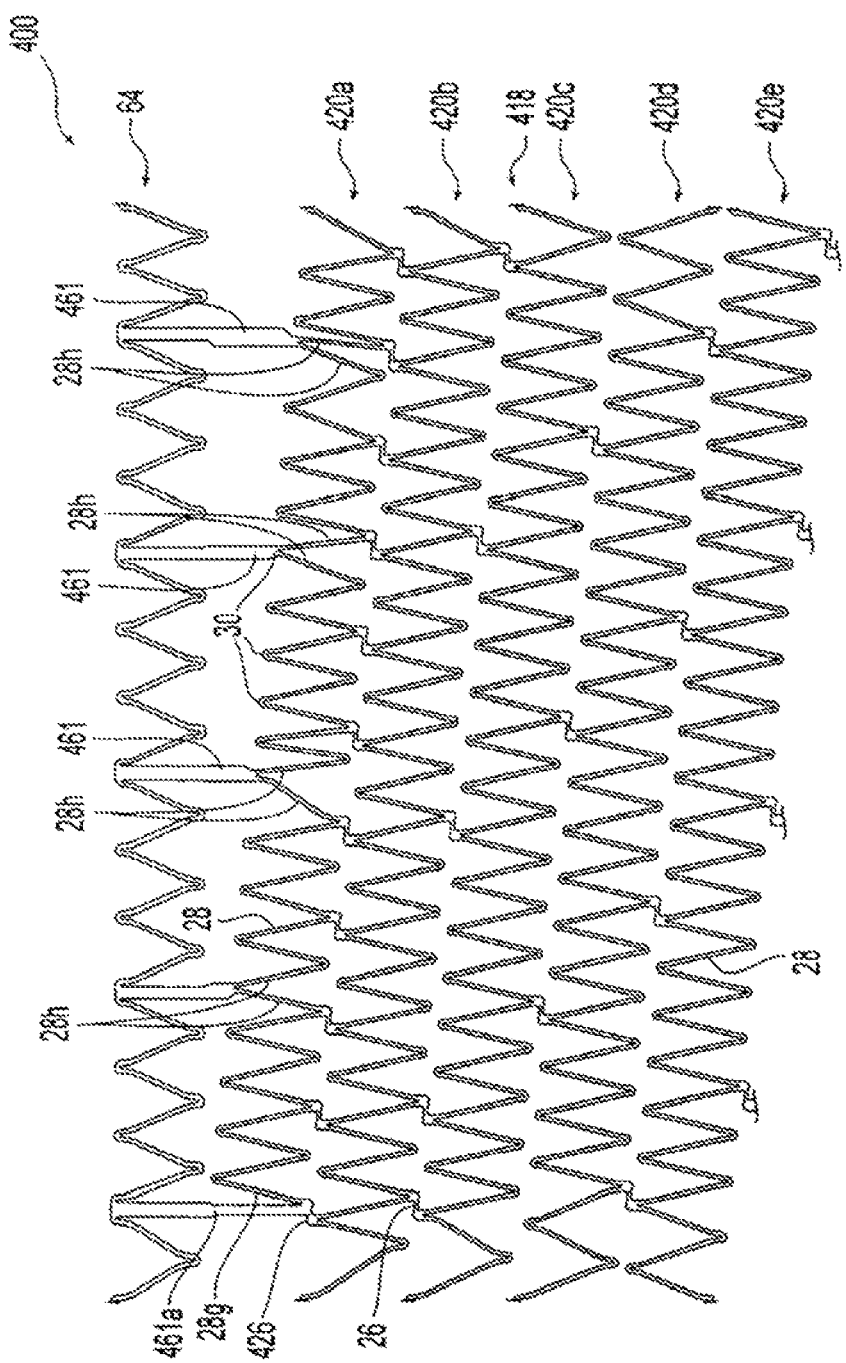
FIG. 13 is an unrolled view of the end of the stent of FIG. 11, with the stent of FIG. 11 longitudinally separated along a cut line and laid unrolled along a flat plane in an expanded configuration.

In a preferred embodiment illustrated in FIGS. 11 and 12, the annular ring 64 of the stent 400 includes extensions 461 that extend in the direction of the axis 16 and connect with the strut vertices 30 of the longitudinally endmost portions of the winding 418. As illustrated in FIGS. 11 and 13, the extensions 461 preferably connect to every third or fourth end-facing strut vertex 30 so that there are six or eight struts 28 disposed between the points where the six extensions 461 connect to the strut vertices 30 at the longitudinal end of the helical winding 418. As also illustrated in FIGS. 11 and 13, the last strut 28g in the helical winding 418 differs (from the other struts 28 that connect to an extension 461) because the last strut 28g is connected to an extension 461a that extends farther from the annular ring 64 than the other extensions 461 and because the last strut 28g connects to join a modified bridge 426 with the corresponding extension 461a FIG. 13 is a view of the stent 400 of FIGS. 11 and 12, but with the stent 400 displayed as if it had been longitudinally cut and laid out in the extended orientation upon a flat plane. As illustrated in FIG. 13, the modified bridge 426 is similar to the bridges 26, but one side of the bridge 426 is connected to an end of the extension 461a.

FIG. 13 also illustrates that certain struts 28 (extension struts 28h) in the endmost circumferential section 420a can have strut lengths that varying in order to allow connection between the extension 461 while maintaining the helical form and spacing 22 of the helical winding 418. As illustrated in FIG. 13, the extension struts 28h can be either longer than or short than the other struts 28 of the stent 400. Furthermore, the extension struts 28h extend these shorter or longer lengths so that the end of the struts 28h extending away from the extensions 461 connect to strut vertices 30 or bridge vertices 31 disposed in line with the spacing 22 defined by the helical winding 418. The variable strut lengths of the extension struts 28h serve, in part, as alignment structures to align extensions 461, which are preferably distributed in a pattern of six equally-distributed locations on the circumference of the annular ring 64, with corresponding strut vertices 30 or the bridge 426 (as illustrated in FIG. 13), which do not always naturally align with the circumferential locations of the extensions 461.

In the embodiment of FIGS. 11-13, the pattern of bridges 26 and struts 28 over the length of the helical winding 418 (i.e., the strut pattern) varies from the end strut 28g proximate the first end 10 to the end strut 28g proximate the second end 12. As illustrated in FIGS. 11 and 13, the strut pattern in the majority of the helical winding 418 is preferably a five-seven pattern, where the number of struts 28 between sequential bridges 26 along the path of the helical winding 418 is a repeating pattern of five and seven, as illustrated at circumferential sections 420c, 420d, and 420e. In the second-to-endmost winding of helical winding 418, at circumferential section 420b, the five-seven pattern preferably changes to a variable pattern of four, three, and one, where additional bridges 26 are added to the stent 400 between circumferential sections 420b and 420a. In the endmost winding of the helical winding 418, at circumferential section 420a, the strut pattern preferably changes again to a four-four pattern where four struts 28 are provided between bridges 26 along the helical path of the circumferential section 420a. In the embodiment illustrated in FIGS. 11-13, the strut 400 can be characterized as having a five-seven pattern with a four-four pattern at each end of the stent 400 where connecting to the first and second ends 10 and 12. As can be appreciated, alternative strut patterns can be employed, with the majority of the intermediate portion 14 having one strut pattern and each end of the intermediate portion 14 having a different pattern, with a single circumferential section 420 disposed between two adjoining patterns to act as a transition between the two strut patterns. The circumferential section 420b preferably acts as a transition between the five-seven pattern and the four-four pattern and thus has a variable pattern that is adjusted to accommodate the transition between alternative adjoining patterns.

It is believed that greater stent flexibility is achieved in the portions of the stent 400 having more struts 28 disposed between bridges 26 (a higher-numbered strut pattern, preferably a five-seven pattern) than in portions having fewer struts 28 between bridges 26 (a lower-numbered strut pattern, preferably a four-four pattern). It is also believed that the ends of the stent 400 are less flexible than the longitudinal middle of the stent 400 because of the additional stiffness provided where the strut pattern changes from high-numbered strut pattern to a lower-numbered strut pattern, preferably changing from a five-seven pattern to a four-four pattern.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. An implantable prosthesis comprising:
a first pattern defining a continuous helical winding having a plurality of circumferential sections circumscribing a longitudinal axis from a first end to a second end, the circumferential sections including a first end circumferential section at the first end and a second end circumferential section at the second end and one or more central circumferential sections therebetween, the circumferential sections being spaced apart along the axis and including a plurality of struts joined together end-to-end, the end-to-end joining of two struts of the plurality of struts defining a vertex between the two struts, at least one of the vertices of the first or second end circumferential sections being an end vertex formed by a joining of two final struts of the first or second end circumferential sections, a plurality of bridges connecting one circumferential section to an adjacent circumferential section; and a second pattern defining an annular ring having a plurality of extensions extending therefrom and connecting to the continuous helical winding, at least one extension connecting to the end vertex, at least one of the two final struts joining together to define the end vertex having an end strut length, the end strut length being different than a range of central strut lengths of the struts of the one or more central circumferential sections.

2. The implantable prosthesis according to claim 1, wherein the first pattern comprises the plurality of bridges having a minimum width greater than a width of any of the plurality of struts.

3. The implantable prosthesis according to claim 1, wherein the first pattern comprises defining the continuous helical winding as a single helical winding.

4. The implantable prosthesis according to claim 1, wherein the first pattern comprises the plurality of bridges extending substantially parallel with respect to the longitudinal axis.

5. The implantable prosthesis according to claim 1, wherein the first pattern comprises forming the plurality of bridges such that at least one of the bridges extends obliquely with respect to an axis extending parallel to the longitudinal axis.

6. The implantable prosthesis according to claim 1, wherein the forming a first pattern comprises forming the plurality of bridges such that at least one of the bridges directly connects a peak of one circumferential section to another peak of an adjacent circumferential section.

7. The implantable prosthesis according to claim 1, wherein the forming a first pattern comprises forming the plurality of bridges such that at least one of the bridges directly connects a peak of one circumferential section to a trough of an adjacent circumferential section.

8. The implantable prosthesis according to claim 1, wherein the forming a first pattern comprises forming the plurality of bridges such that at least one of the bridges directly connects a trough of one circumferential section to a trough of an adjacent circumferential section.

9. The implantable prosthesis according to claim 1, wherein the forming a first pattern comprises forming the plurality of struts to have a width of approximately 80% of a width of the plurality of bridges.

* * * * *